United States Patent [19]

Oyama et al.

[11] Patent Number: 5,206,149
[45] Date of Patent: Apr. 27, 1993

[54] METHOD OF HIGH SENSITIVITY LUMINESCENCE ANALYSIS

[75] Inventors: Yoshihiro Oyama, Kanagawa; Shuntaro Hosaka, Tokyo; Tetsuya Makino, Kanagawa, all of Japan

[73] Assignee: Toray Industries, Inc., Tokyo, Japan

[21] Appl. No.: 623,426

[22] PCT Filed: Apr. 27, 1990

[86] PCT No.: PCT/JP90/00558

§ 371 Date: Feb. 5, 1991

§ 102(e) Date: Feb. 5, 1991

[87] PCT Pub. No.: WO90/13665

PCT Pub. Date: Nov. 15, 1990

[30] Foreign Application Priority Data

Apr. 28, 1989 [JP] Japan .................. 1-109598
Sep. 5, 1989 [JP] Japan .................. 1-229575
Feb. 19, 1990 [JP] Japan .................. 2-37997

[51] Int. Cl.$^5$ .............. C12Q 1/68; C12Q 1/28; G01N 53/00; G01N 21/52

[52] U.S. Cl. .............................. 435/28; 435/6; 435/25; 435/7.72; 435/5; 252/301.17; 536/18.1; 514/212; 540/524

[58] Field of Search ........... 435/28, 25, 7.72, 6, 435/5; 536/18.1; 252/301.17; 514/212; 540/524

[56] References Cited

U.S. PATENT DOCUMENTS

| | | | |
|---|---|---|---|
| 3,928,227 | 12/1975 | Sena et al. ............... | 252/301.17 |
| 3,957,677 | 5/1976 | Tarkkanen ............... | 252/301.17 |
| 4,193,983 | 3/1980 | Ullman et al. ........... | 435/7.72 |
| 4,256,834 | 3/1981 | Zuk et al. ................ | 435/5 |
| 4,624,799 | 11/1986 | Hegge et al. ............ | 252/301.17 |
| 4,681,883 | 7/1987 | Brown et al. ............ | 540/524 |
| 4,729,950 | 3/1988 | Kricka et al. ........... | 435/28 |
| 4,835,101 | 5/1989 | Kao et al. ................ | 435/25 |
| 4,842,997 | 6/1989 | Carter et al. ............ | 435/28 |
| 4,853,327 | 8/1989 | Dattagupta ............. | 435/28 |
| 4,950,588 | 8/1990 | Dattagupta ............. | 435/28 |

FOREIGN PATENT DOCUMENTS 0087959 7/1983 European Pat. Off. .

Primary Examiner—Michael G. Wityshyn
Assistant Examiner—Louise N. Leary
Attorney, Agent, or Firm—Birch, Stewart, Kolasch & Birch

[57] ABSTRACT

This invention relates to a method of high sensitivity luminescence analysis using, as an enhancer, 2-hydroxy-9-fluorenone, the compound expressed by the following formula

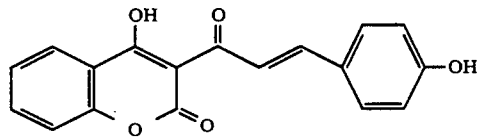

or an oxazole compound expressed by the formula

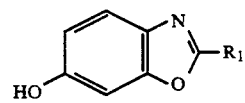

[I]

in the formula $R_1$ representing hydrogen, $C_nH_{2n+1}$ (here, n representing a positive integer of 1 to 4), $XC_nH_{2n}$ (here, X representing F, Cl, Br or I, and n representing a positive integer of 1 to 4), $C_nH_{2n+1}CO_2$ (n being as defined above), a phenyl group, a naphthyl group, $C_nH_{2n+1}C_6H_4$ (n being as defined above), $YC_6H_4$ (Y representing F, Cl, Br, I or a phenyl group) or $XYC_6H_3$ (X and Y being as defined above).

14 Claims, 20 Drawing Sheets

METHOD OF HIGH SENSITIVITY LUMINESCENCE ANALYSIS

BACKGROUND OF THE INVENTION

1. Technical Field

This invention relates to a method of high sensitivity analysis through chemiluminescence measurement in use of enzymatic reactions, antigen-antibody reactions and nucleic acid hybridization in the areas of clinical laboratory testing, food inspection, environmental analysis, inspection of animals and plants, and manufacturing process control checking.

2. Background Art

The luminescent reaction using oxidation of luminol, isoluminol or a derivative thereof [abbreviated as chemiluminescent DPD (2,3-dihydro-1,4-phthalazinedione) in the following] by a peroxidase is used for immunoassay, analysis of elastase, analysis of glucose and analysis of oxidants. It is known that for improving the luminescent intensity of said luminescent reaction, it is effective to add an enhancer, such as those shown below, to the reaction system.

(1) 6-Hydroxybenzothiazole (Patent Publication No. SHO 56-5000252)
(2) A certain kind of phenol having a substitution group (Patent Publication No. SHO 59-171839)
(3) A certain kind of aromatic amine (Patent Publication No. SHO 61-54453)

However, such enhancers have the following difficulties.

The enhancer (1) is generally of lower luminescence intensity and smaller signal-to-background ratio.

The typical enhancer of the class (2) is p-iodophenol. Its luminescent signal is high, but the background is also high, therefore the signal-to-background ratio is relatively low.

In the case of the typical enhancer of the class (3) or N,N,N',N'-tetramethylbenzidine, the rise to the luminescent peak is slow, and much time is required for measurement.

For the reaction mechanism of the enhancer effect, there are reports proposing the requirement of efficient formation of luminol semiquinone radical [Thorpe, G. H. C. and Kricka, L. J., "Bioluminescence and Chemiluminescence: New Perspectives," Scholmerich, J., Andreesn, R., Kapp, A., Ernst, M. and Woods, W. G. (Eds), John Wiley, Chichester, pp. 199-208 (1987)] and the requirement of efficient formation of phenoxy radical [Hodgson, M. and Jones, P., Journal of Bioluminescence and Chemiluminescence, Vol. 3, pp. 21-25 (1989)].

However, the phenol derivatives include a number of compounds which do not show an enhancer effect, and it is difficult to choose an effective enhancer based upon the foregoing theories.

Also, for detection or quantification of a gene in a virulent microorganism, a prostaglandin or any other physiologically active substance, luteinizing hormone (LH) and other anterior pituitary hormones, and cytokines such as interleukin in blood, it is required to make a determination based on very small amount in body fluid. Thus, a high sensitivity detection system was called for, and for improvement of the detection sensitivity, an enhancer of higher efficiency has been desired.

SUMMARY OF THE INVENTION

An object of the present invention is to provide a method of high sensitivity luminescent analysis which is characteristically carried out in the presence of a novel enhancer.

Another object of the present invention is to provide a novel oxazole derivative which is effective as an enhancer and allows the luminescent analysis to be carried out with an enhancer of higher efficiency than the conventional enhancers used.

In detecting or determining a substance in use of the chemiluminescence produced through reaction of (a) a peroxidase or a derivative thereof, (b) an oxidant and (c) luminol or isoluminol, or a derivative thereof, the present invention relates to a method of high sensitivity luminescent analysis characterized in that the luminescence inducing reaction is carried out in the presence of at least one compound chosen from the group comprised of 2-hydroxy-9-fluorenone, the compound expressed by the following formula

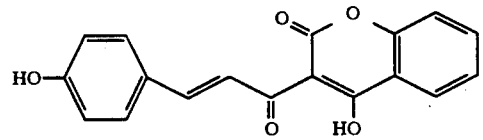

and oxazole derivatives expressed by the formula

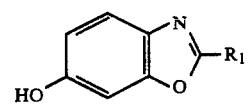

[I]

in the formula, $R_1$ representing hydrogen, $C_nH_{2n+1}$ (here, n representing a positive integer of 1 to 4), $XC_nH_{2n}$ (here, X representing F, Cl, Br or I; n being as defined in the foregoing), $C_nH_{2n+1}CO_2$ (n being as defined in the foregoing), phenyl group, naphthyl group, $C_nH_{2n+1}C_6H_4$ (n being as defined in the foregoing), $YC_6H_4$ (Y representing F, Cl, Br, I or phenyl group), or $XYC_6H_3$ (X and Y being as defined in the foregoing).

DETAILED DESCRIPTION OF THE INVENTION

Figure 1:
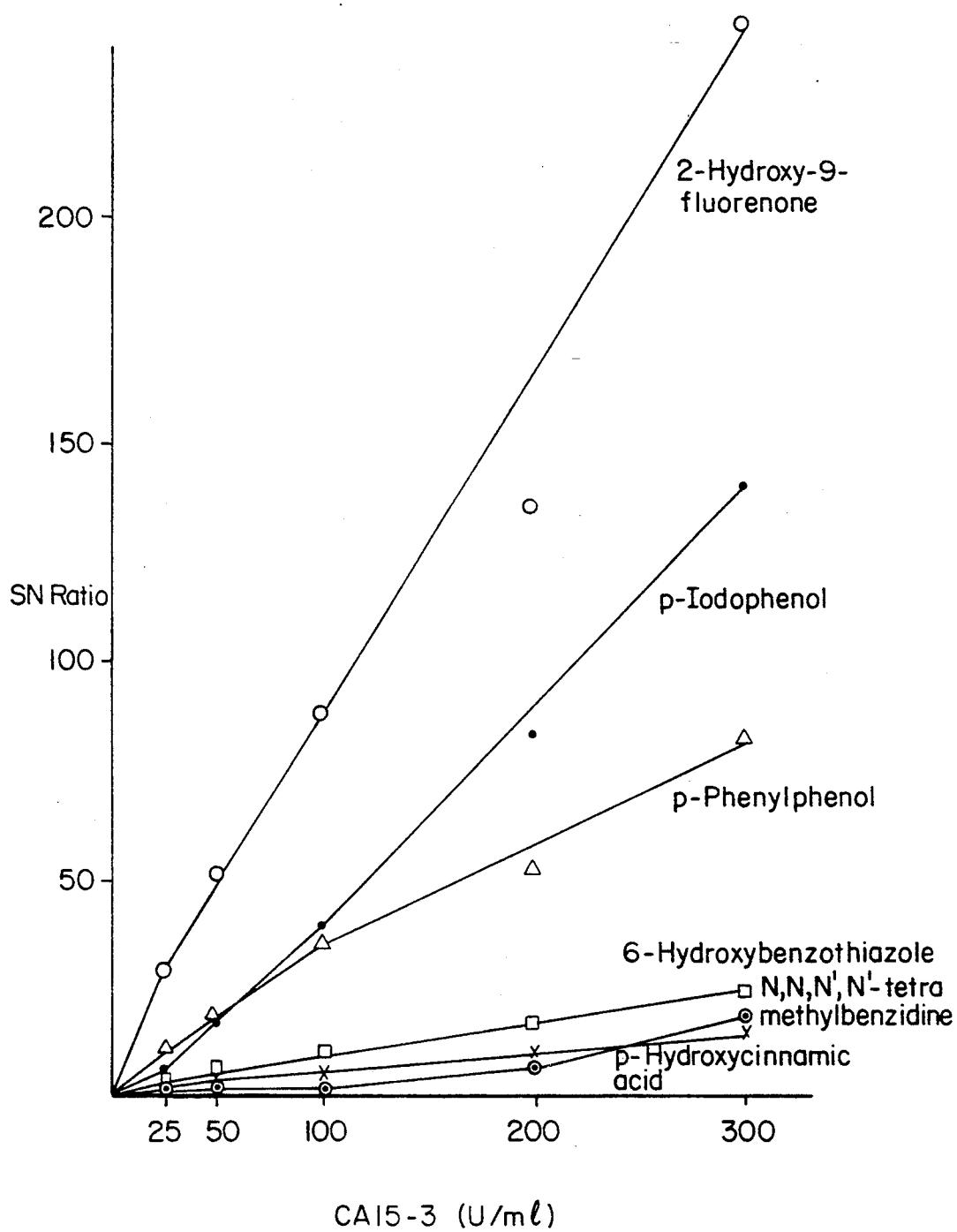
FIGS. 1 and 2 show the results of analysis of CA15-3 with an enhancer of the present invention, or 2-hydroxy-9-fluorenone, compared against those with the conventional enhancers used, FIG. 1 showing the SN ratios of luminescent intensity after 5 seconds and FIG. 2 showing those after 10 seconds.

The chemiluminescence enhancing effect of the enhancer of the present invention, or 2-hydroxy-9-fluorenone,

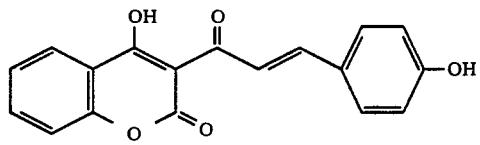

4-hydroxy-3-[3-(4-hydroxyphenyl)-1-oxo-2-propenyl]-2H-1-benzopyrane-2-one (abbreviated as HHBP in the following) or an oxazole derivative expressed by formula [I] can be confirmed as the luminescent signal-to-background ratio obtainable in the peroxidase/oxidant/chemiluminescent DPD system is greatly improved when the enhancer of the present invention is added to the system. The term "background" used here refers to the luminescent intensity in the absence of the peroxidase or derivative thereof.

The peroxidase used according to the present invention is not particularly limited but is preferably a plant peroxidase such as horse radish peroxidase. For the peroxidase derivative, there may be listed, for example, a peroxidase-antibody conjugate, peroxidase-antigen conjugate, peroxidase-streptoavidin conjugate and biotin bonded peroxidase. The antibody used here is not particularly limited, but there may be preferably used such partial structures as Fab' and F(ab)$_2$ in addition to intact IgG and IgM. The antigen is also not limited, and low molecular haptens such as fluorescein and steroid hormone and high molecular substances such as polypeptides, proteins and polysaccharides are also usable.

For the nucleic acid hybridization, linear and cyclic DNA and RNA of 10 or more bases are usable.

As an oxidant, hydrogen peroxide is preferably used, but perborates and hypochlorites are also usable.

The chemiluminescent DPD used according to the present invention includes luminol, isoluminol and N-(4-aminobutyl)-N-ethylisoluminol, and antigens, antibodies and nucleic acids bonded thereto. Of these, luminol is particularly preferable.

HHBP used as an enhancer according to the present invention can be produced through condensation of 3-acetyl-4-hydroxycumarin and para-hydroxybenbenzoaldehyde in the presence of an amine, according to the method described in the patent publication No. Sho 50-46666.

As described in the foregoing, the present invention relates to a method of high sensitivity luminescent analysis which is characteristically carried out in the presence of an oxazole derivative expressed by the formula

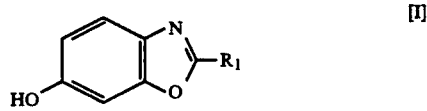

in the formula, R$_1$ representing hydrogen C$_n$H$_{2n+1}$ (here, n representing a positive integer of 1 to 4), XC$_n$H$_{2n}$ (here, X representing F, Cl, Br or I, and n being as defined above), C$_n$H$_{2n+1}$CO$_2$ (n being as defined above), C$_n$H$_{2n+1}$C$_6$H$_4$ (n being as defined above), phenyl group, naphthyl group, YC$_6$H$_4$ (Y representing F, Cl, Br, or a phenyl group) or XYC$_6$H$_3$ (X and Y being as defined above).

Specifically, for R$_1$ in the compound [I] of the present invention, there may be listed hydrogen and, as alkyl group of the carbon atom number of 1 to 4, such groups as methyl, ethyl, propyl (n- and iso-), butyl (n-, iso-, sec- and tert-) and phenyl.

Also, for the halogenated alkyl group, there may be listed such groups as fluoromethyl, 1-chloromethyl, bromomethyl, iodomethyl, 1-fluoroethyl, 2-fluoroethyl, 1-chloroethyl, 2-chloroethyl, 1-bromoethyl, 2-bromoethyl, 1-iodoethyl, 2-iodoethyl, 1-fluoropropyl, 2-fluoropropyl, 3-fluoropropyl, 1-fluoro-1-methylethyl, 2-fluoro-1-methylethyl, 1-chloropropyl, 2-chloropropyl, 3-chloropropyl, 1-chloro-1-methylethyl, 2-chloro-1-methylethyl, 1-bromopropyl, 2-bromopropyl, 3-bromopropyl, 1-bromo-1-methylethyl, 2-bromo-1-methylethyl, 1-iodopropyl, 2-iodopropyl, 3-iodopropyl, 1-iodo-1-methylethyl, 2-iodo-1-methylethyl, 1-fluoropropyl, 2-fluorobutyl, 3-fluorobutyl, 4-fluorobutyl, 1-fluoro-1-methylpropyl, 2-fluoro-1-methylpropyl, 3-fluoro-1-methylpropyl, 1-fluoromethylpropyl, 1-fluoro-2-methylpropyl, 2-fluoro-2-methylpropyl, 3-fluoro-2-methylpropyl, 1-fluoromethyl-1,1-dimethylmethyl, 1-chlorobutyl, 2-chlorobutyl, 3-chlorobutyl, 4-chlorobutyl, 1-chloro-1-methylpropyl, 2-chloro-1-methylpropyl, 3-chloro-1-methylpropyl, 1-chloromethylpropyl, 1-chloro-2-methylpropyl, 2-chloro-2-methylpropyl, 3-chloro-2-methylpropyl, 1-chloromethyl-1,1-dimethylmethyl, 1-bromobutyl, 2-bromobutyl, 3-bromobutyl, 4-bromobutyl, 1-bromo-1-methylpropyl, 2-bromo-1-methylpropyl, 3-bromo-1-methylpropyl, 1-bromomethylpropyl, 1-bromo-2-methylpropyl, 2-bromo-2-methylpropyl, 3-bromo-2-methylpropyl, 1-bromomethylmethyl-1,1-dimethylmethyl, 1-iodobutyl, 2-iodobutyl, 3-iodobutyl, 4-iodobutyl, 1-iodo-1-methylpropyl, 2-iodo- 1-methylpropyl, 3-iodo-1-methylpropy, 1-iodo-2-methylpropyl, 2-iodo-2-methylpropyl, 3-iodo-2-methylpropyl and 1-iodomethyl-1,1-dimethylmethyl.

For the alkoxycarbonyl group, there may be listed such groups as methoxycarbonyl, ethoxycarbonyl, propoxycarbonyl, 1-methylethoxycarbonyl, butoxycarbonyl, 1-methylpropoxycarbonyl, 2-methylpropoxycarbonyl and 1,1-dimethylethoxycarbonyl.

For the alkyl substituted phenyl group, there may be listed such groups as 2-methylphenyl, 3-methylphenyl, 4-methylphenyl, 2-ethylphenyl, 3-ethylphenyl, 4-ethylphenyl, 2-propylphenyl, 3-propylphenyl, 4-propylphenyl, 2-(1-methylethyl), 3-(1-methylethyl), 4-(1-methylethyl), 2-butylphenyl, 3-butylphenyl, 4-butylphenyl, 2-(1-methylpropyl)phenyl, 3-(1-methylpropyl)phenyl, 4-(1-methylpropyl)phenyl, 2-(2-methylpropyl)phenyl, 3-(2-methylpropyl)phenyl, 4-(2-methylpropyl)phenyl, 2-(1,1-dimethylethyl)phenyl, 3-(1,1-dimethylethyl)phenyl and 4-(1,1-dimethylethyl)phenyl.

For the halogen substituted phenyl group, there may be listed such groups as 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2-iodophenyl, 3-iodophenyl and 4-iodophenyl.

For the disubstituted phenyl group, there may be listed such groups as 2,4-dichlorophenyl and 3,5-dichlorophenyl.

Of these, preferable substitution groups are hydrogen, methyl group, phenyl group, chloromethyl group, ethoxycarbonyl group, 2-methylphenyl group, 3-bromophenyl group, 4-chlorophenyl group and 2,4-dichlorophenyl group.

Of the compounds expressed by the formula [I], any oxazole derivative expressed by the formula

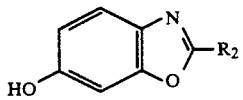

[II]

in the formula, $R_2$ representing $XC_nH_{2n}$ (here, X representing F, Cl, Br or I, and n representing a positive integer of 1 to 4), $C_nH_{2n+1}CO_2$ (n being as defined above), $C_nH_{2n+1}C_6H_4$ (n being as defined above), naphthyl group, $YC_6H_4$ (Y representing F, Cl, Br, or I or a phenyl group) $XYC_6H_3$ (X and Y being as defined above), is a novel substance.

The compound [I] of the present invention can be produced by synthesis according to the reaction formula

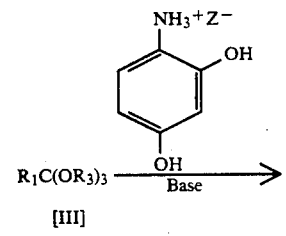

[III]

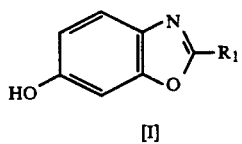

[I]

in the formula, $R_1$ representing hydrogen, $C_nH_{2n+1}$ (here, n representing a positive integer of 1 to 4), $XC_nH_{2n}$ (here, X representing F, Cl, Br or I and n being as defined above), $C_nH_{2n+1}CO_2$ (n being as defined above), phenyl group, naphthyl group, $C_nH_{2n+1}C_6H_4$ (n being as defined above), $YC_6H_4$ (Y representing F, Cl, Br, I or a phenyl group) or $XYC_6H_3$ (X and Y being as defined above); $R_3$ representing $C_nH_{2n+1}$ (n being as defined above); and Z representing F, Cl, Br or I.

Here, $R_1$ used in the compound [III] is the same as $R_1$ used in the compound [I].

Also, for the alkyl group $R_3$, there may be listed such groups as methyl, ethyl, propyl, 1-methylethyl, butyl, 1-methylpropyl, 2-methylpropyl and 1,1-dimethylethyl.

The base used according to the present invention includes carbonates such as sodium hydrogencarbonate, potassium hydrogencarbonate, sodium carbonate and potassium carbonate, amines such as trimethylamine, triethylamine and t-butylamine, and aromatic heterocyclic compounds such as pyridine and quinoline, but sodium hydrogencarbonate is particularly preferable.

The reaction does not require a solvent and proceeds at a temperature of 20° to 150° C., but for enhancing the yield of the objective product, a temperature of 50° to 120° C. is preferable.

The oxazole compound [I] may also be produced, when $R_1$ is $XC_nH_{2n}$ (X representing F, Cl, Br or I, and n representing a positive integer of 1 to 4), according to the formula (2), or when $R_1$ is $YC_6H_4$ (Y representing F, Cl, Br, I or a phenyl group), according to the formula (3), set forth below.

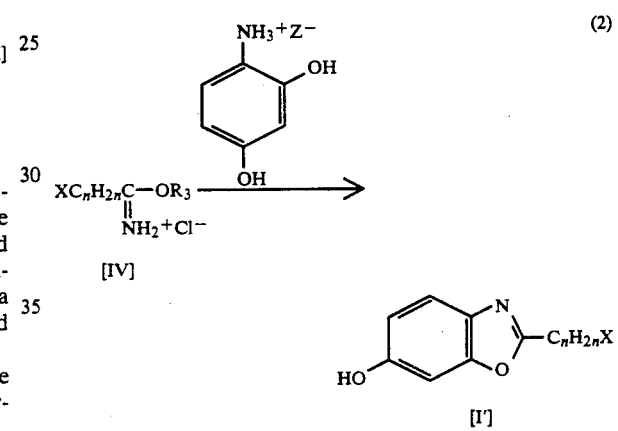

[IV]

[I']

in the formula, $R_3$ representing $C_nH_{2n+1}$ (n representing a positive integer of 1 to 4), and X and Z representing F, Cl, Br or I respectively.

For the halogenated alkyl group used in the compound [IV], the same halogenated alkyl group as that used in the compound [I] may be used. Also, for $R_3$ used in the compound [IV], the same $R_3$ as that used in the compound [III] may be used.

The reaction solvent used according to the present invention includes alcohols such as methanol, ethanol, propanol and butanol, ethers such as ethyl ether and THF, and aprotic polar solvents such as DMF and DMSO. Of these, ethanol is particularly preferable.

The reaction proceeds at a temperature of 20° to 150° C., but for increasing the yield of the objective product, a temperature of 60° to 90° C. is preferable.

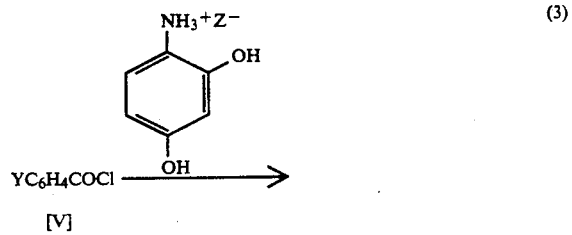

[V]

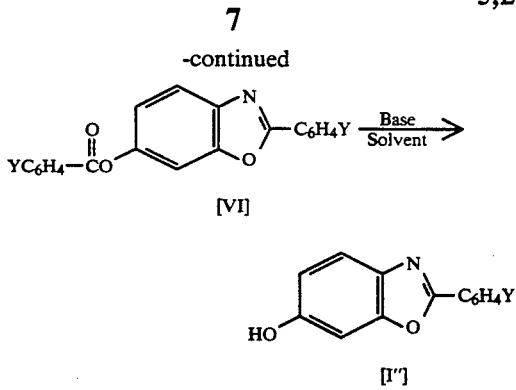

in the formula, Y representing F, Cl, Br, I or a phenyl group, and Z representing F, Cl, Br or I.

For the substituted phenyl group used in the compound [V], the halogenated phenyl group or phenylphenyl group used in the compound [I] may be used.

The first stage of the reaction does not require a solvent and proceeds at a temperature of 100° to 280° C., but for enhancing the yield of the compound [VI], a temperature of 150° to 250° C. is preferable.

The base used for hydrolytic reaction of the compound [VI] includes sodium hydroxide. potassium hydroxide and sodium carbonate, but sodium hydroxide is particularly preferable. For the solvent, water, alcohols such as methanol and ethanol and ethers such as THF are usable, but a mixture of water/ethanol is particularly preferable.

The hydrolytic reaction proceeds at a temperature of 20° to 50° C., but for enhancing the yield of the object, a temperature of 25° to 35° C. is preferable.

The enhancer of the present invention is usable for determination of a substance in use of a luminescent system comprising a peroxidase, chemiluminescent DPD and oxidant but is preferably usable for determination through enzymatic immunoassay and DNA hybridization.

The present invention will now be described in detail with reference to nonlimiting examples.

The reagents and apparatus used in the examples are as described below.

Reagents

4-Aminoresorcinol hydrochloride and chloroacetonitile were purchased from the Aldrich Co.; ethanol, DMSO, diethyl oxalate, 3-bromobenzoyl chloride, 2-methylbenzoyl chloride, 4-chlorobenzoyl chloride, 2,4-dichlorobenzoyl chloride, luminol (5-amino-2,3-dihydro-1,4-phthalazinedione and isoluminol (6-amino-2,3-dihydro-1,4-phthalazinedione) purchased from the Tokyo Kasei Co.; phosphorus pentachloride and sodium hydrogencarbonate purchased from the Kanto Kagaku Co.; hydrogen chloride cylinder purchased from the Tsurumi Soda Co.; N-(4-aminobutyl)-N-ethylisoluminol (ABEI) and tris(hydroxymethyl)aminomethane purchased from the Sigma Chemical Co.; horse radish peroxidase (HRP) purchased from the Boehringer Mannheim GmbH; powder PBS purchased from the Nissui Seiyaku Co.; bovine serum albumin (BSA) purchased from the Seikagaku Kogyo Co.; and 2-hydroxy-9-fluorenone purchased from the Aldrich Chemical Co.

HHBP was prepared according to the method described in Patent Publication No. SHO 50-46666.

Mammary cancer related antigen (CA15-3) and anti-CA15-3 antibody (mouse monoclonal antibody) were provided by Centocor (Malvern, USA). The horse radish peroxidase labeled anti-CA15-3 antibody was prepared by the maleimide hinge method [Yoshitake, S. et al., J. Biochem., 92, 1413–1424 (1982)] and isolated and purified by Pharmacia's FPLC using a hydroxy-apatite column (Mitsui-Toatsu, HCA-column, $\phi$7.6 mm×L100 mm).

Anti-CA15-3 antibody coated polystyrene beads were prepared by immersing 6 mm diameter polystyrene beads (Meiwa Fusso Shokai, surface roughness #80) in a 10 μg/ml PBS solution of anti-CA15-3 antibody overnight.

Analytical Apparatus

The chemiluminescent reaction was carried out in a disposable 3 ml plastic tube of 12 mm$\phi$×47 mm. The generated light was detected by a luminometer (Biolumat LB9500T), a product of the Berthold Co.

The infrared spectrum (abbreviated as IR in the following) was measured by an FT/IR-5000, product of the Nippon Bunko Kogyo Co.

The nuclear magnetic resonance spectrum (abbreviated as NMR in the following) was measured by an EX90FTNMR, product of the Nippon Denshi Co.

The mass spectrum (abbreviated as MS in the following) was measured by the direct introduction method using a JMS D300 spectrograph. The high resolution MS was determined with a JMS DX-303 spectrograph.

EXAMPLE 1

Luminescent assay of peroxidase in use of luminol and 2-hydroxy-9-fluorenone

200 μl of luminol (100 mM DMSO solution 10 μl/10 ml 0.1 M tris-hydrochloride buffer solution, pH 7.5), 200 μl of 2-hydroxy-9-fluorenone (100 mM DMSO solution 10 μl/10 ml 0.1 M tris-hydrochloride buffer solution, pH 7.5), 10 μl of HRP [100,000 times dilution of 1111 unit/mg with a PBS buffer solution containing 1 g/l of BSA (pH 7.4)], and 10 μl of hydrogen peroxide (1000 times dilution of a 9.1 M aqueous solution) were introduced into a plastic cuvette, and the mixture was stirred for 3 seconds with a vortex mixer, and the luminescent intensity after 10 seconds was measured. Next, 10 μl of a PBS buffer solution containing no HRP (pH 7.4) and the foregoing amounts of luminol, 2-hydroxy-9-fluorenone and hydrogen peroxide were mixed and stirred, and the luminescent intensity after 10 seconds was measured. The ratio of the former to the latter is shown as a signal-to-background ratio (SN ratio) in Table 1.

EXAMPLE 2

The procedure of Example 1 was repeated with isoluminol used in place of luminol. The result is shown in Table 1.

EXAMPLE 3

The procedure of Example 1 was repeated with N-(4-amino-butyl)-N-ethylisoluminol used in place of luminol. The result is shown in Table 1.

REFERENCES 1 TO 3

The procedures of Examples 1, 2 and 3 were followed except that 2-hydroxy-9-fluorenone was not used. The results are also shown in Table 1.

TABLE 1

Signal-to-background ratio (SN ratio) with
2,3-dihydro-1,4-phthalazinedione (DPD)

| | DPD | Luminescent intensity after 10 seconds (relative value) | | |
|---|---|---|---|---|
| | | +HRP | −HRP | SN ratio |
| Example 1 | Luminol | 449863 | 103 | 4368 |
| Example 2 | Isoluminol | 9885 | 99 | 99.8 |
| Example 3 | N-(4-aminobutyl)-N-ethylisoluminol | 17370 | 96 | 180.9 |
| Reference 1 | Luminol | 149 | 133 | 1.12 |
| Reference 2 | Isoluminol | 167 | 154 | 1.08 |
| Reference 3 | N-(4-aminobutyl)-N-ethylisoluminol | 157 | 137 | 1.15 |

EXAMPLE 4

Luminescent assay of CA15-3 antigen with
2-hydroxy-9-fluorenone and various enhancers used Diluting a CA15-3 antigen solution (615 U/ml) with a phosphate buffer solution (PBS) containing bovine serum albumin into solutions of the concentrations of 300 U/ml, 200 U/ml, 100 U/ml, 50 U/ml, 25 U/ml and 0 U/ml (PBS containing bovine serum albumin), these were taken as standard CA15-3 solutions.

Two samples of each of the standard CA15-3 solutions of the foregoing concentrations were poured into the wells of a tray (25 wells), each in 20 µl. Then, 300 µl of a peroxidase labeled anti-CA15-3 antibody (mouse) was added to the respective wells. To each well, an antibody coated bead having the adhering liquid soaked up with filter paper was added with a pincette.

Applying a tray cover seal, the tray was lightly tapped for admixture of the components in the respective wells, and each mixture was allowed to react at 25° C. for 2 hours. After completion of the reaction, the beads were washed 3 times, each time with 5 ml of physiological saline, with a bead washer used. After washing, each bead in the tray was transferred to a test tube then to a plastic cuvette for measurement with a luminometer.

200 µl of luminol solution (100 mM DMSO solution 10 µl/10 ml 0.1 M tris-hydrochloride buffer solution, pH 7.5), 200 µl of 2-hydroxy-9-fluorenone solution (100 mM DMSO solution 10 µl/10 ml 0.1 M tris-hydrochloride buffer solution, pH 7.5) and 10 µl of hydrogen peroxide solution (1000 times dilution of a 9.1 M aqueous solution) were added to each plastic cuvette, and the luminescent intensities after 5 and 10 seconds were measured. The results are shown in Tables 2-1 and 2-2.

Figure 2:
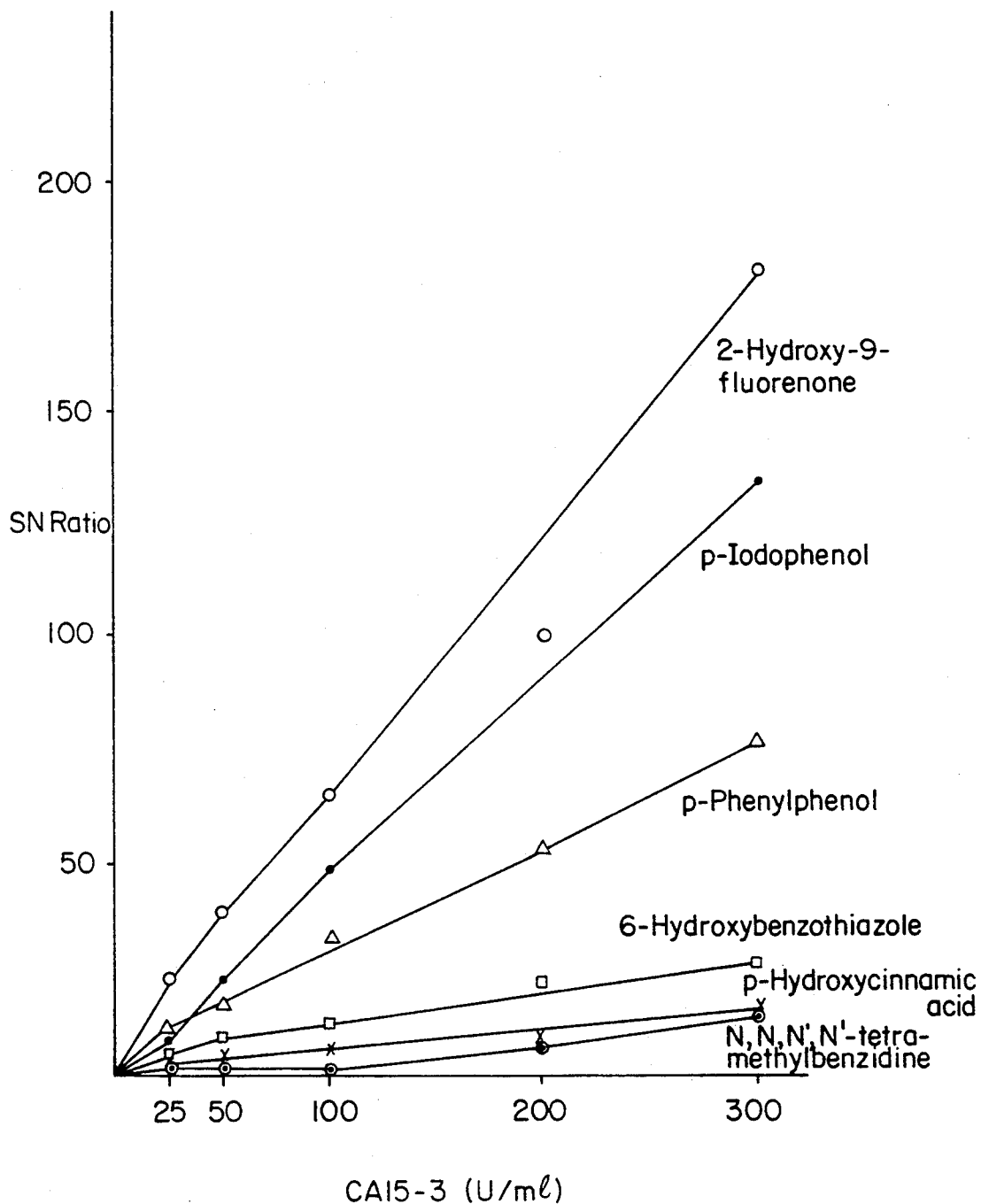

The ratios of the luminescent intensities after 5 and 10 seconds of the standard CA15-3 antigen solutions (300 U/ml, 200 U/ml, 100 U/ml, 50 U/ml and 25 U/ml) to those after 5 and 10 seconds of 0 U/ml (SN ratios) were obtained, as shown in FIGS. 1 and 2.

REFERENCES 4 TO 8

The procedure of Example 4 was followed with p-iodophenol, p-hydroxycinnamic acid, p-phenylphenol, 6-hydroxybenzothiazole and N,N,N',N'-tetramethylbenzidine used in place of 2-hydroxy-9-fluorenone. The luminescent intensities are shown in Tables 2-1 and 2-2, and the SN ratios shown in FIGS. 1 and 2.

TABLE 2-1

Luminescent intensities after 5 seconds with various enhancers added (relative values)

| | Enhancers | CA15-3 (U/ml) | | | | | |
|---|---|---|---|---|---|---|---|
| | | 0 | 25 | 50 | 100 | 200 | 300 |
| Reference 4 | p-Iodophenol | 1686 | 10314 | 28463 | 67438 | 142810 | 238017 |
| Reference 5 | p-Hydroxycinnamic acid | 1745 | 4661 | 7736 | 10314 | 17851 | 28246 |
| Reference 6 | p-Phenylphenol | 590 | 7023 | 10525 | 21541 | 31672 | 49180 |
| Reference 7 | 6-Hydroxybenzothiazole | 912 | 3471 | 6843 | 9719 | 15868 | 22810 |
| Reference 8 | N,N,N',N'-tetramethylbenzidine | 203 | 99 | 174 | 298 | 1785 | 3968 |
| Example 4 | 2-Hydroxy-9-fluorenone | 472 | 13554 | 24492 | 41803 | 64033 | 116066 |

TABLE 2-2

Luminescent intensities after 10 seconds with various enhancers added (relative values)

| | Enhancers | CA15-3 (U/ml) | | | | | |
|---|---|---|---|---|---|---|---|
| | | 0 | 25 | 50 | 100 | 200 | 300 |
| Reference 4 | p-Iodophenol | 1796 | 12664 | 38123 | 85089 | 153034 | 242580 |
| Reference 5 | p-Hydroxycinnamic acid | 1630 | 4670 | 7663 | 10363 | 15525 | 27940 |
| Reference 6 | p-Phenylphenol | 675 | 7003 | 10487 | 21288 | 35650 | 52421 |
| Reference 7 | 6-Hydroxybenzothiazole | 811 | 3438 | 6819 | 9696 | 18092 | 22644 |
| Reference 8 | N,N,N',N'-tetramethylbenzidine | 423 | 84 | 354 | 290 | 3127 | 6900 |
| Example 4 | 2-Hydroxy-9-fluorenone | 643 | 13652 | 24248 | 40907 | 63885 | 116905 |

EXAMPLE 5

Luminescent assay of peroxidase in use of luminol and HHBP

200 µl of luminol solution (100 mM DMSO solution 10 µl/10 ml 0.1 M tris-hydrochloride buffer solution, pH 8.5), 200 µl of HHBP solution (100 mM DMSO solution 10 µl/10 ml 0.1 M tris-hydrochloride buffer solution, pH 8.5), 10 µl of horse radish peroxidase (HRP) solution (100,000 times dilution of 1111 unit/mg with a PBS buffer solution (pH 7.0) containing 1 g/l of BSA) and 10 µl of hydrogen peroxide solution (1000 times dilution of a 9.1 M aqueous solution) were introduced into a plastic tube and stirred for 3 seconds with a vortex mixer, then the luminescent intensity after 1 minute was measured.

Next, 10 µl of the buffer solution (pH 7.0) not containing HRP and the foregoing amounts of luminol, HHBP and hydrogen peroxide solution were mixed and stirred, and the luminescent intensity after 1 minute was measured. The ratio of the former to the latter is shown as signal-to-background ratio (SN ratio) in Table 3.

EXAMPLES 6 AND 7

As Examples 6 and 7, the luminescent intensities were measured similarly to Example 5 except that isoluminol (Example 6) and ABEI (Example 7) were used in place of luminol in Example 5, as shown in Table 3.

REFERENCES 9 TO 11

Luminescent intensities were measured similarly to Examples 5 to 7 except that HHBP was not used, as shown in Table 3.

From Examples 5 to 7 and References 9 to 11, it has become apparent that the method of the invention is a distinguished method of luminescence analysis.

TABLE 3

Signal-to-background ratios (SN ratios) with 2,3-dihydro-1,4-phthalazinedione (DPD)

| | DPD | Luminescent intensity after 1 minute (relative value) | | |
|---|---|---|---|---|
| | | +HRP | −HRP | SN ratio |
| Example 5 | Luminol | 453039 | 88 | 5148 |
| Example 6 | Isoluminol | 7524 | 24 | 313.5 |
| Example 7 | ABEI | 21073 | 31 | 679.8 |
| Reference 9 | Luminol | 550 | 507 | 1.08 |
| Reference 10 | Isoluminol | 160 | 137 | 1.17 |
| Reference 11 | ABEI | 188 | 180 | 1.04 |

EXAMPLE 8

Synthesis of 6-hydroxybenzoxazole 2.0 g of 4-aminoresorcinol hydrochloride (12.4 mmol), 8.5 ml of methyl orthoformate (51.4 mmol) and 1.07 g of sodium hydrogencarbonate (12.8 mmol) were introduced into a two-necked flask provided with a cooling condenser, and the mixture was stirred in argon atmosphere at 100° C. for a whole day and night. After completion of the reaction, the reaction solution was cooled. Then, hexane was added, and the reaction product was filtered. The crystal was washed with water to remove the inorganic salt then filtered again.

The obtained crystal was dissolved in acetone, and with activated carbon added, the solution was refluxed with heat for 1.5 hours. Removing the activated carbon, and evaporating acetone the obtained crystal was re-crystallized with acetone-water. There was obtained 0.28 g of a white powder. The reaction yield was 16.7%.

m.p.: 183.5° to 185.2° C.

IR (KBr, cm$^{-1}$): 3150, 1630, 1528, 1489, 1276, 1236, 1195, 1104, 1085, 816

NMR ($\delta$, DMSO-$d_6$) 6.81 (dd, 1H), 7.03 (d, 1H), 7.53 (d, 1H), 8.46 (s, 1H), 9.75 (s, 1H)

MS (EI): 135 (M+), 52, 31

High resolution MS (EI): $C_7H_5O_2N$: Calclulated: 135.0344. Observed 135.0332.

Luminescent assay of peroxidase in use of luminol and 6-hydroxybenzoxazole

200 μl of a luminol solution (100 mM DMSO solution 10 μl/10 ml, 0.1 M tris-hydrochloride buffer solution, pH 8.5), 200 μl of a 6-hydroxybenzoxazole solution (100 mM DMSO solution 10 μl/10 ml, 0.1 M tris-hydrochloride buffer solution, pH 8.5), 10 μl of a horse radish peroxidase (HRP) solution (10,000 times dilution of 1111 unit/mg with a PBS buffer solution (pH 7.0) containing 1 g/l of BSA) and 10 μl of a hydrogen peroxide solution (1000 times dilution of a 9.1 M aqueous solution) were introduced into a plastic cuvette and stirred for 3 seconds with a vortex mixer used, then the luminescent intensity after 1 minute was measured.

Next, 10 μl of the buffer solution not containing HRP and the foregoing amounts of luminol, 6-hydroxybenzoxazole and hydrogen peroxide solution were mixed and stirred, and the luminescent intensity after 1 minute was measured. The ratio of the former to the latter is shown as signal-to-background ratio (SN ratio) in Table 4.

EXAMPLES 9 AND 10

As Examples 9 and 10, the luminescent intensities were measured similarly to Example 8 except that isoluminol (Example 9) and N-(4-aminobutyl)-N-ethylisoluminol (abbreviated as ABEI in the following) (Example 10) were used in place of luminol in the luminescent assay in Example 8, as shown in Table 4.

EXAMPLE 11

The luminescent intensity was measured similarly to Example 8 except that 2-methyl-6-hydroxybenzoxazole was used in place of 6-hydroxybenzoxazole in Example 8, as shown in Table 4.

EXAMPLES 12 AND 13

As Examples 12 and 13, the luminescent intensities were measured similarly to Example 11 except that isoluminol (Example 12) and ABEI (Example 13) were used in place of luminol in Example 11, as shown in Table 4.

EXAMPLE 14

The luminescent intensity was measured similarly to Example 8 with 2-phenyl-6-hydroxybenzoxazole used in place of 6-hydroxybenzoxazole in Example 8, as shown in Table 4.

EXAMPLES 15 AND 16

The luminescent intensities were measured similarly to Example 14 except that isoluminol (Example 15) and ABEI (Example 16) were used in place of luminol in Example 14, as shown in Table 4.

REFERENCES 12 TO 14

As References 12 to 14, the luminescent intensities were measured similarly to Examples 8 to 10 except that 6-hydroxybenzoxazole was not used, as shown in Table 4.

TABLE 4

Signal-to-background ratios through combination of enhancers and 2,3-dihydro-1,4-phthalazinedione (DPD)

| | Enhancer | DPD | Luminescent intensity after 1 minute (relative value) | | |
|---|---|---|---|---|---|
| | | | +HRP | −HRP | SN ratio |
| Example 8 | 6-Hydroxybenzoxazole | Luminol | 664522 | 81 | 8204.0 |
| Example 9 | 6-Hydroxybenzoxazole | Isoluminol | 10277 | 25 | 411.1 |

TABLE 4-continued

Signal-to-background ratios through combination of enhancers and 2,3-dihydro-1,4-phthalazinedione (DPD)

| | | | Luminescent intensity after 1 minute (relative value) | | |
|---|---|---|---|---|---|
| | Enhancer | DPD | +HRP | −HRP | SN ratio |
| Example 10 | 6-Hydroxybenzoxazole | ABEI | 26481 | 26 | 1018.5 |
| Example 11 | 2-Methyl-6-hydroxybenzoxazole | Luminol | 975682 | 78 | 12508.7 |
| Example 12 | 2-Methyl-6-hydroxybenzoxazole | Isoluminol | 15028 | 28 | 536.7 |
| Example 13 | 2-Methyl-6-hydroxybenzoxazole | ABEI | 46109 | 26 | 1773.4 |
| Example 14 | 2-Phenyl-6-hydroxybenzoxazole | Luminol | 2764970* | 82 | 33719.1* |
| Example 15 | 2-Phenyl-6-hydroxybenzoxazole | Isoluminol | 54033 | 50 | 1080.7 |
| Example 16 | 2-Phenyl-6-hydroxybenzoxazole | ABEI | 92167 | 50 | 1843.3 |
| Reference 12 | None | Luminol | 622 | 357 | 1.7 |
| Reference 13 | None | Isoluminol | 459 | 193 | 2.4 |
| Reference 14 | None | ABEI | 1371 | 226 | 6.1 |

*Value measured with HRP diluted 10 times and the luminescent intensity after 1 minute multiplied 10 times.

EXAMPLE 17

Luminescent assay of CA15-3 antigen in use of HHBP

A CA15-3 antigen solution (615 U/ml) was diluted with a phosphate buffer solution (PBS) containing bovine serum albumine into solutions of the concentrations of 300 U/ml, 200 U/ml, 100 U/ml, 50 U/ml, 25 U/ml and 0 U/ml (PBS containing bovine serum albumine), and these were taken as standard CA15-3 solutions.

Two samples of each of the standard solutions of the foregoing concentrations were introduced into the wells of a tray (25 wells), each in 20 μl. To each well, 300 μl of a peroxidase labeled marker anti-CA15-3 antibody (mouse) was added. Then, an antibody coated bead having the adhering liquid soaked up with filter paper was added to each well.

Applying a tray cover seal and lightly tapping for mixing, the reaction was carried out at 25° C. for 2 hours. After completion of the reaction, the mixture was washed 3 times with 5 ml of physiological saline in a bead washer. After washing, each bead in the tray was transferred to a test tube then to a plastic tube for measurement with a luminometer.

Adding 200 μl of luminol solution (100 mM DMSO solution 10 μl/10 ml 0.1 M tris-hydrochloride buffer solution, pH 7.5), 200 μl of HHBP solution (100 mM DMSO solution 10 μl/ml 0.1 M tris-hydrochloride buffer solution, pH 7.5) and 10 μl of hydrogen peroxide solution (1000 times dilution of a 9.1 M aqueous solution) to the respective plastic tubes, the luminescent intensities after 10 seconds were measured. Mean luminescent intensities of two samples are shown in Table 5.

Figure 3:
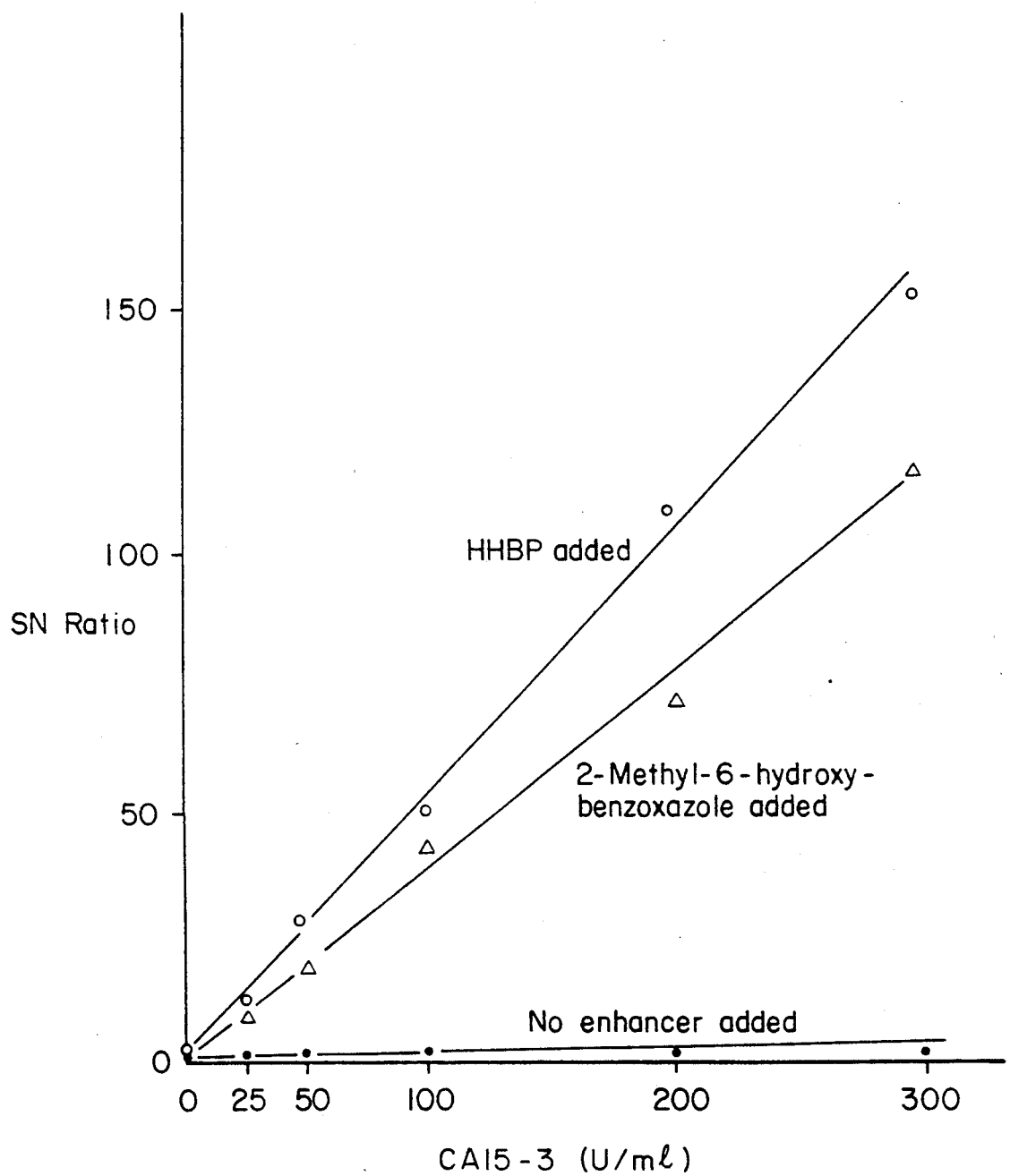
FIG. 3 shows the results of analysis of CA15-3 with and without addition of the enhancer of the invention to the luminescent system.

The ratios of the mean luminescent intensities after 10 seconds of the standard CA15-3 antigen solutions (300 U/ml, 200 U/ml, 100 U/ml, 50 U/ml and 25 U/ml) to the mean luminescent intensity after 10 seconds of 0 U/ml (SN ratios) were obtained, as shown in FIG. 3.

EXAMPLE 18

Luminescent assay of CA15-3 antigen in use of 2-methyl-6-hydroxybenzoxazole

Following the procedure of Example 17 except for the use of 2-methyl-6-hydroxybenzoxazole in place of HHBP in Example 17 the luminescent intensities were measured. The mean luminescent intensities are shown in Table 5, and the SN ratios shown in FIG. 3.

REFERENCE 15

Following the procedure of Example 17 except that HHBP and 2-methyl-6-hydroxybenzoxazole were not used, the measurement was made similarly. The mean luminescent intensities are shown in Table 5, and the SN ratios shown in FIG. 3.

TABLE 5

Analysis of CA15-3: Mean luminescent intensities after 10 seconds (relative values)

| | | CA15-3 (U/ml) | | | | | |
|---|---|---|---|---|---|---|---|
| | Enhancer | 0 | 25 | 50 | 100 | 200 | 300 |
| Example 17 | HHBP | 602 | 8031 | 17045 | 30454 | 65824 | 91745 |
| Example 18 | 2-Methyl-6-hydroxybenzoxazole | 401 | 3370 | 6929 | 17223 | 27926 | 46613 |
| Reference 15 | None | 154 | 148 | 165 | 165 | 152 | 182 |

EXAMPLE 19

Synthesis of 2-chloromethyl-6-hydroxybenzoxazole 26.1 g (345.7 mmol) of chloroacetonitrile, 20 ml of absolute ethanol, and 70 ml of ether were introduced into a three-necked 300 ml flask provided with stirring vanes, and while stirring gently, hydrogen chloride gas was blown into the flask at room temperature for about 40 minutes. A white precipitate was produced which was then filtered and washed with ether. There was obtained 37.5 g (237.3 mmol) of ethyl chloromethylimidate hydrochloride. The yield of the reaction was 68.7%.

1.78 g (11.3 mmol) of said ethyl chloromethylimidate hydrochloride, 1.22 g (7.55 mmol) of 4-aminoresorcinol hydrochloride, and 20 ml of ethanol were introduced into a two-necked flask provided with a Dimroth condenser, and the mixture was refluxed with heat in argon atmosphere for a whole day and night. After completion of the reaction and cooling, the crystal was filtered and washed with hexane, then the object was vacuum dried. There was obtained 0.40 g (2.33 mmol) of 2- chloromethyl-6-hydroxybenzoxazole, and the yield of the reaction was 30.9%.

m.p.: 148.5° to 153.7° C.

Figure 4:
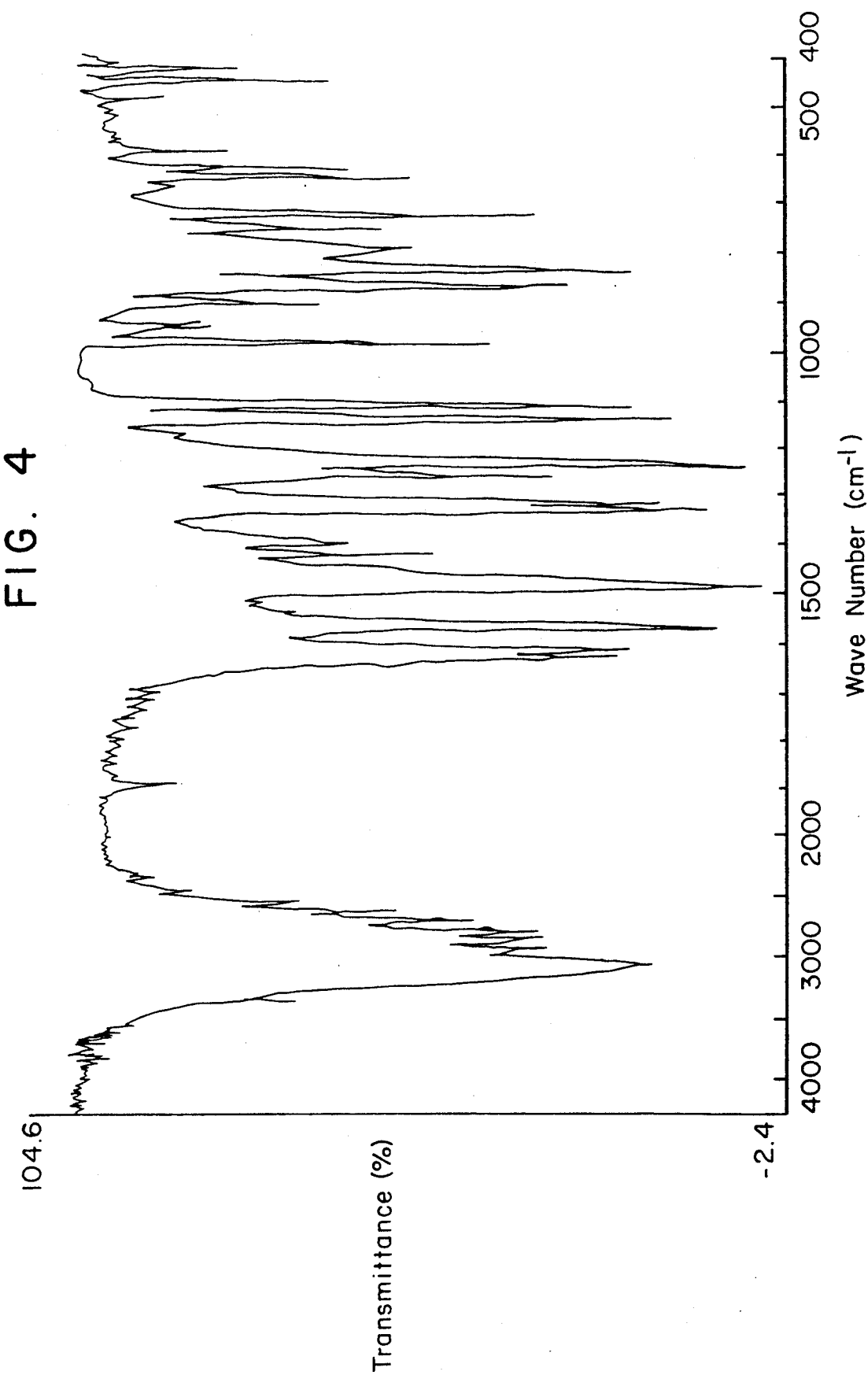
FIG. 4 is an IR spectrum of 2-chloromethyl-6-hydroxybenzoxazole obtained in Example 19.

IR (FIG. 4, KBr, cm$^{-1}$): 3076, 1615, 1572, 1491, 1334, 1238, 1141, 837

Figure 5:
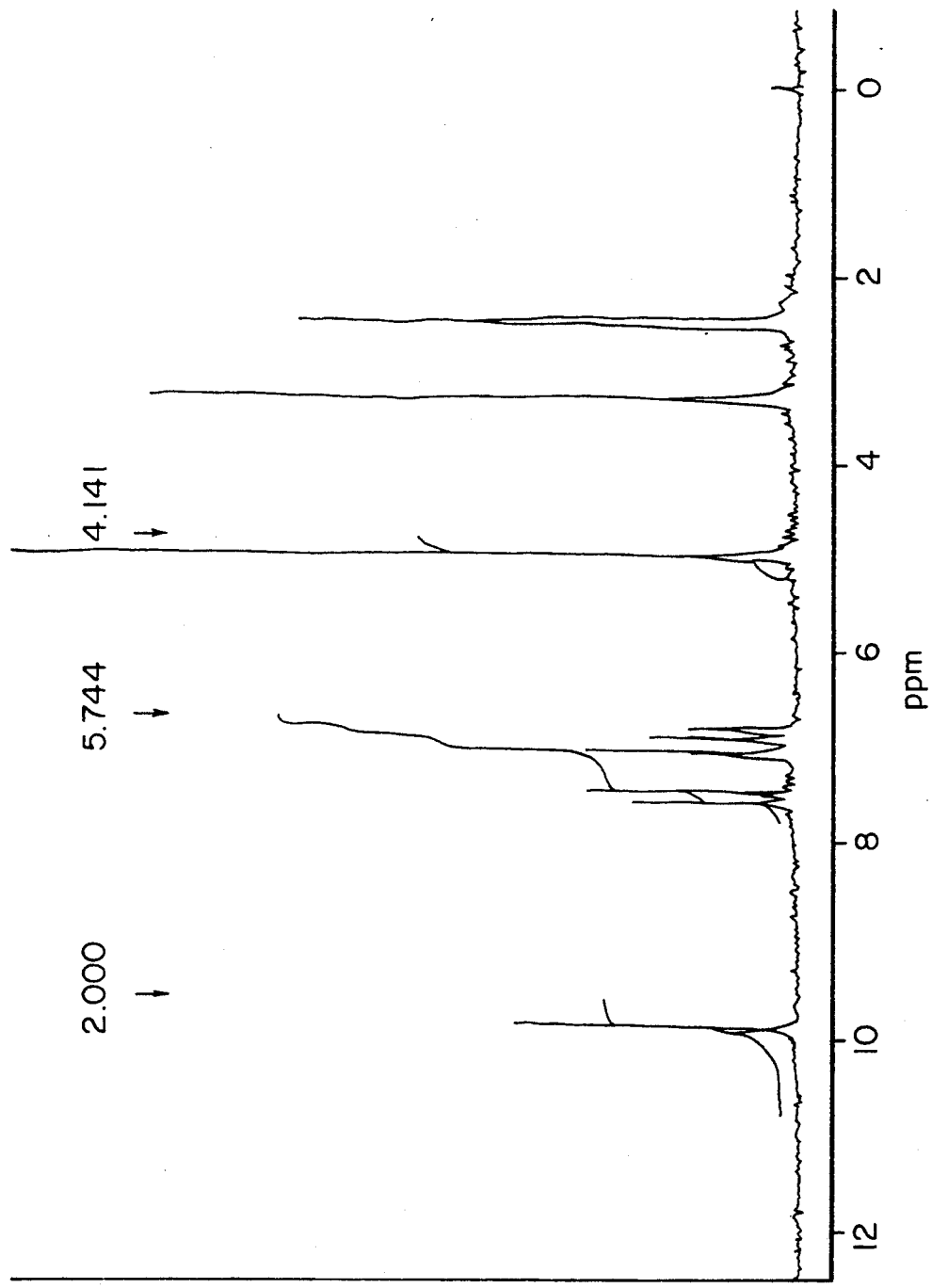
FIG. 5 is an NMR spectrum of the same.

NMR (FIG. 5, DMSO-d$_6$) 4.97 (s, 2H), 6,84 (dd, 2H), 7.08 (d, 1H), 7.55 (d, 1H), 9.89 (s, 1H)

MS (EI): 183 (M ), 148

High resolution MS (EI): C$_8$H$_6$O$_2$NCl: Calculated: 183.0015. Observed 183.0051.

EXAMPLE 20

Synthesis of 2-ethoxycarbonyl-6-hydroxybenzoxazole 61.3 g (420 mmol) of diethyl oxalate and 90.2 g (433 mmol) of phosphorous pentachloride were introduced into a three-necked 500 ml flask provided with stirring vanes and a cooling condenser and were stirred with heat at 105° C. for 17 hours.

The remaining liquid was vacuum distilled under 11 mmHg, and 53.2 g (265 mmol) of the fraction distilling at 77° to 85° C. were collected. The yield of dichloroethoxyethyl acetate was 63.0%.

85 ml of dehydrated ether, 35.5 ml of absolute ethanol and 53.2 g (265 mmol) of dichloroethoxyethyl acetate were introduced into a three-necked 500 ml flask provided with stirring vanes, a cooling condenser and a dropping funnel in argon atmosphere, and while stirring, 49.5 ml of dehydrated pyridine were added dropwise from the dropping funnel over 1 hour.

After stirring at room temperature for 2 hours, pyridine hydrochloride was removed by filtering and washed with 50 ml of dehydrated ether. Distilling off ether from the filtrate, the remaining solution was stirred at 90° C. for 1.5 hours. The reaction solution was cooled, ether was added, and the solution was washed with 3N-sulfuric acid and then an aqueous solution of sodium hydrogencarbonate. Drying the ether layer with magnesium sulfate and distilling off ether, the remaining solution was vacuum distilled at 7 mmHg, and there was collected 40.1 g (182 mmol) of the fraction distilling at 83° to 89° C. The yield of produced triethoxyethyl acetate was 68.7%.

Taking 4 ml of said triethoxyethyl acetate, 1.00 g (6.19 mmol) of 4-aminoresorcinol hydrochloride and 5.05 mg of sodium hydrogencarbonate, they were introduced into a two-necked flask provided with a cooling condenser under argon atmosphere, and the mixture was stirred with heat at 100° C. for a whole day and night.

The reaction solution was cooled to produce a precipitate which was then filtered. Dissolving the precipitate in acetone, and adding activated carbon, the solution was refluxed with heat for 1.5 hours. Filtering out the activated carbon, the filtrate was run through a silica gel column for concentration. The produced crystal was vacuum dried, and there was obtained 1.07 g (5.17 mmol) of 2-ethoxycarbonyl-6-hydroxybenzoxazole. The yield of the product was 83.5%.

m.p.: 199.5° to 200.2° C.

Figure 6:
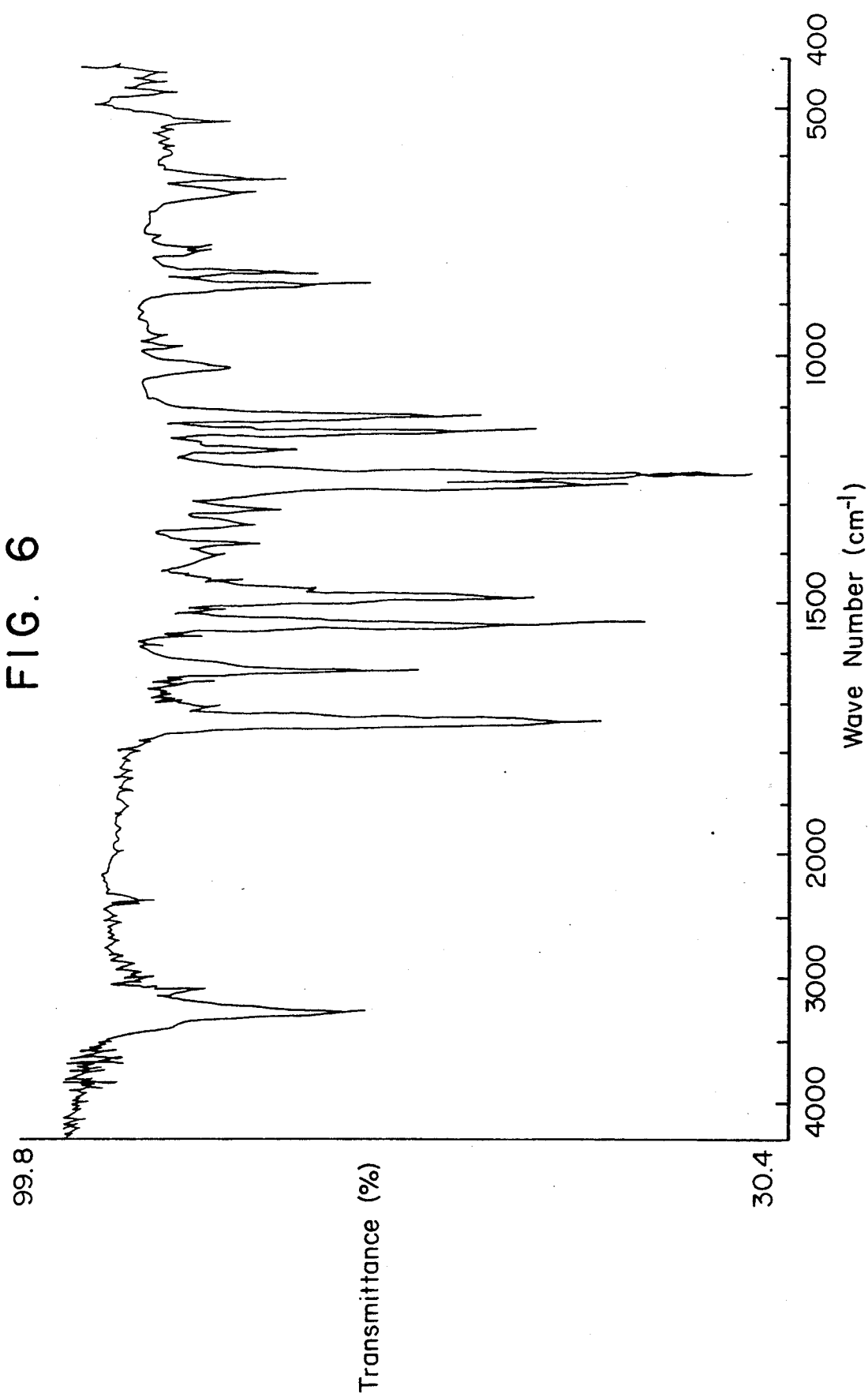
FIG. 6 is an IR spectrum of 2-ethoxycarbonyl-6-hydroxybenzoxazole obtained in Example 20.

IR (FIG. 6, KBr, cm$^{-1}$): 3278, 1736, 1630, 1539, 1489, 1261, 1241, 1145, 116, 849

Figure 7:
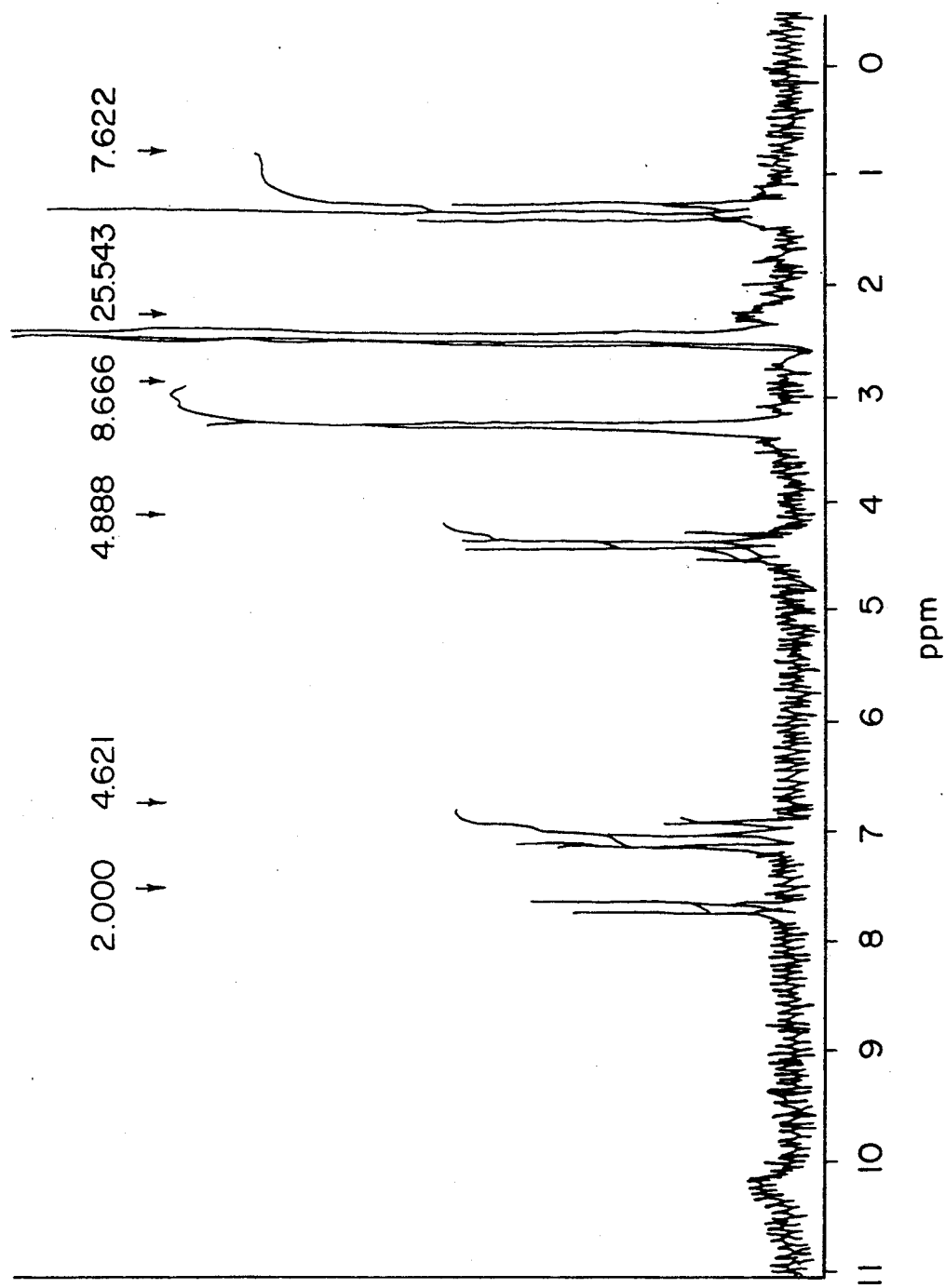
FIG. 7 is an NMR spectrum of the same.

NMR (FIG. 7, DMSO-d$_6$): 1.35 (t, 3H), 4.41 (q, 2H), 6.97 (dd, 1H), 7.14 (d, 1H), 7.72 (d, 1H), 10.25 (bs, 1H)

MS (EI): 207 (M+) 135

High resolution MS (EI): C$_{10}$H$_9$O$_4$N: Calculated: 207.0591. Observed 207.0561.

EXAMPLE 21

Synthesis of 2-(3-bromophenyl)-6-hydroxybenzoxazole 14.1 ml (107 mmol) of 3-bromobenzoic chloride and 1.7 g (10.5 mmol) of 4-aminoresorcinol hydrochloride were introduced into a three-necked flask provided with a thermometer and a cooling condenser, and the mixture was heated at 90° to 145° C. for 30 minutes. To the residue, an aqueous solution of sodium hydroxide and methanol were added into a homogeneous solution which was then stirred at room temperature for 2 hours. The reaction solution was extracted twice with ethyl acetate and washed with 1N hydrochloric acid then with a saturated sodium chloride solution. Distilling off the excessive ethyl acetate, the obtained precipitate was recrystallized with THF/water. There was obtained 0.68 g (2.35 mmol) of 2-(3-bromophenyl)-6-hydroxybenzoxazole, and the yield was 16.6%.

m.p.: 248.0° to 248.5° C.

Figure 8:
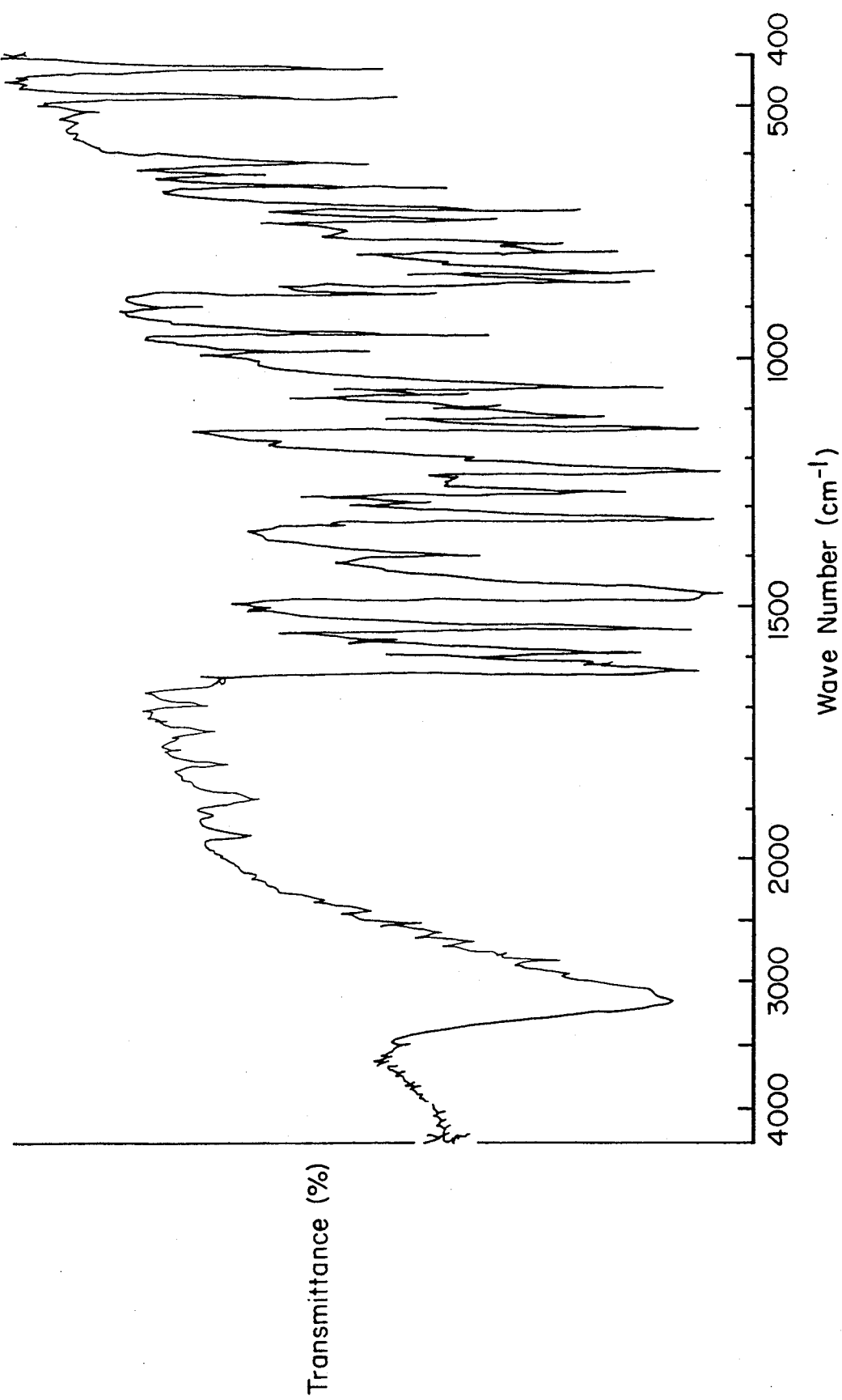
FIG. 8 is an IR spectrum of 2-(3-bromophenyl)-6-hydroxybenzoxazole obtained in Example 21.

IR (FIG. 8, KBr cm$^{-1}$): 3190, 1630, 1549, 1475, 1325, 1234, 1143, 1062, 835

Figure 9:
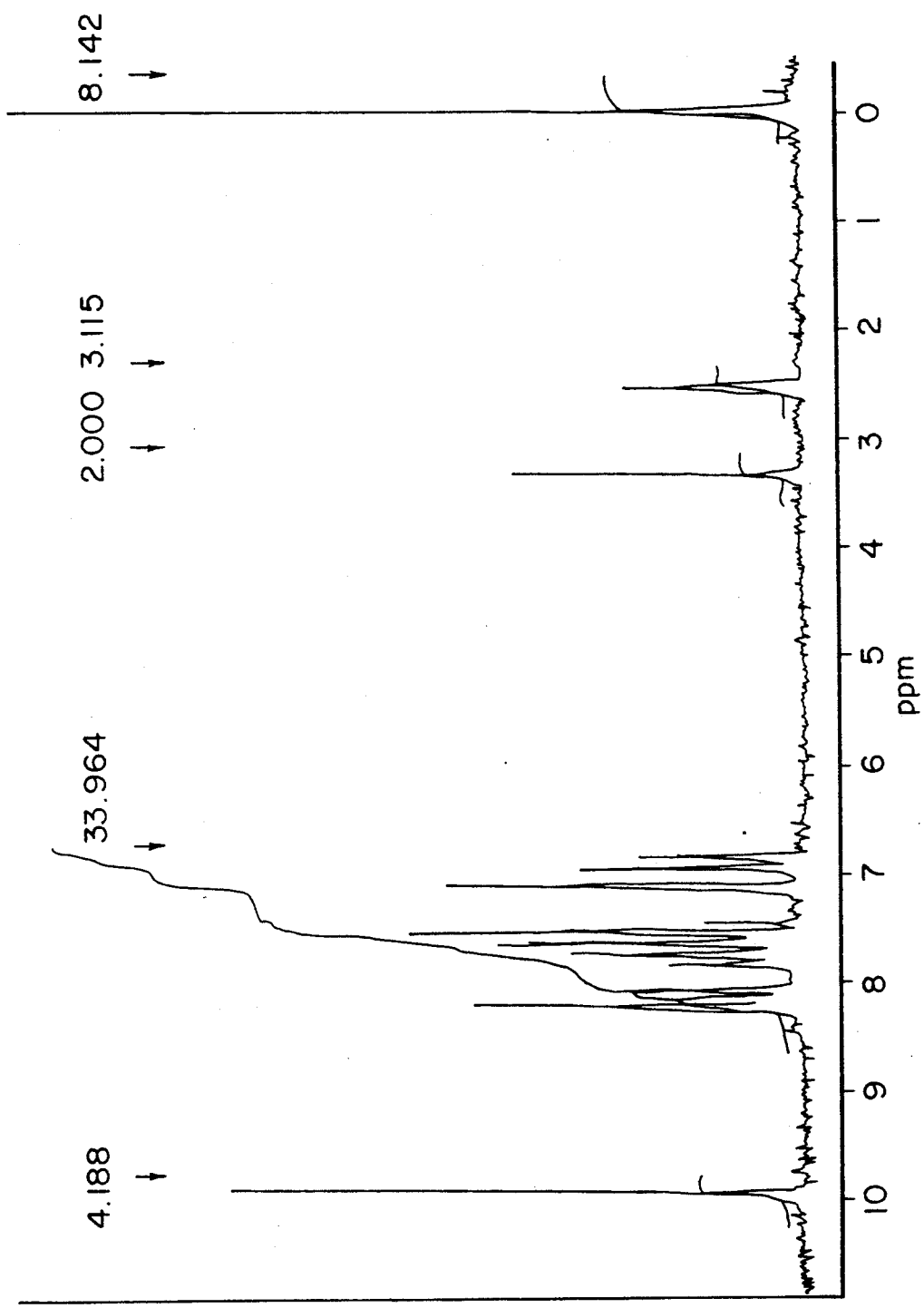
FIG. 9 is an NMR spectrum of the same.

NMR (FIG. 9, DMSO-d$_6$): 6.90 (dd, 1H), 7.12 (d, 1H), 7.66 (m, 2H), 7.71 (d, 1H), 8.15 (m, 2H), 9.94 (s, 1H)

MS (EI): 289 (M+), 291 (M++2), 210, 182

High resolution MS (EI): C$_{13}$H$_8$O$_2$NBr: Calculated: 288.9738. Observed 288.9711.

EXAMPLE 22

Synthesis of 2-(2-methylphenyl)-6-hydroxybenzoxazole 14 ml (107.3 mmol) of 2-methylbenzoyl chloride and 1.7 g (10.5 mmol) of 4-aminoresorcinol hydrochloride were introduced into a three-necked flask provided with a thermometer and a cooling condenser, and the mixture was heated at 144° to 215° C. for 1 hour. Removing the excessive acid chloride by distillation, the system was vacuumed to 1 to 1.5 mmHg, and the fraction distilling at 88° to 230° C. was collected. It was 6.2 g.

With ethanol added, the foregoing fraction was recrystallized, and there was obtained 2.32 g (6.76 mmol) of the crystal. To 500 mg (1.46 mmol) of the crystal, 772 mg (13.6 mmol) of KOH, 30 ml of THF, 5 ml of water and 10 ml of methanol were added, and the mixture was stirred at room temperature for a whole day and night. The reaction solution was extracted with ethyl acetate, the extract was washed with saturated sodium chloride solution, and ethyl acetate was distilled off. Upon drying the residue under reduced pressure, there was obtained 320 g of (1.42 mmol) of 2-(2-methylphenyl)-6-hydroxybenzoxazole. The yield was 62.7%.

m.p.: 133.5° to 137.5° C.

Figure 10:
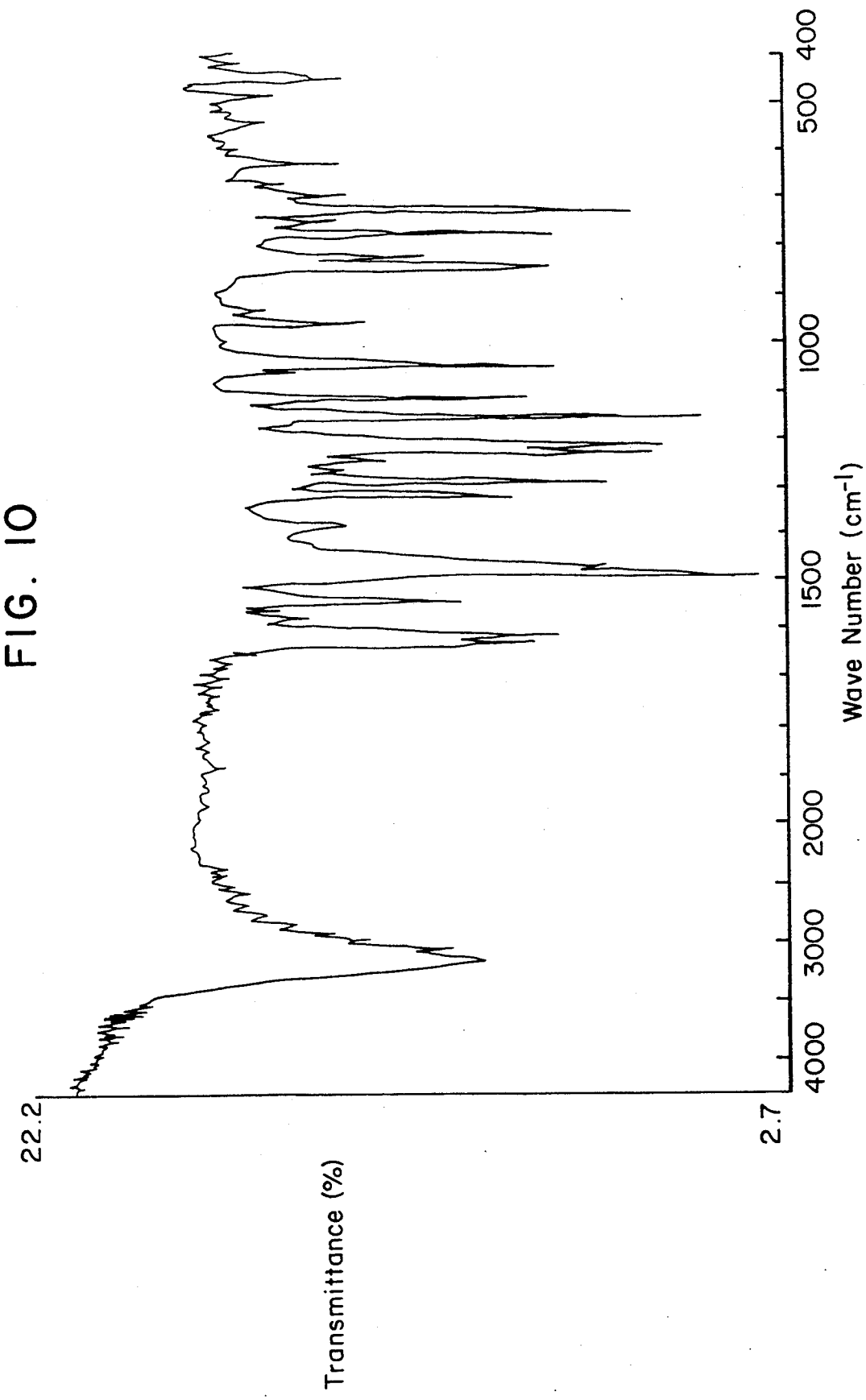
FIG. 10 is an IR spectrum of 2-(2-methylphenyl)hydroxybenzoxazole obtained in Example 22.

IR (FIG. 10, KBr, cm$^{-1}$): 3064, 1613, 1489, 1224, 1151, 729

Figure 11:
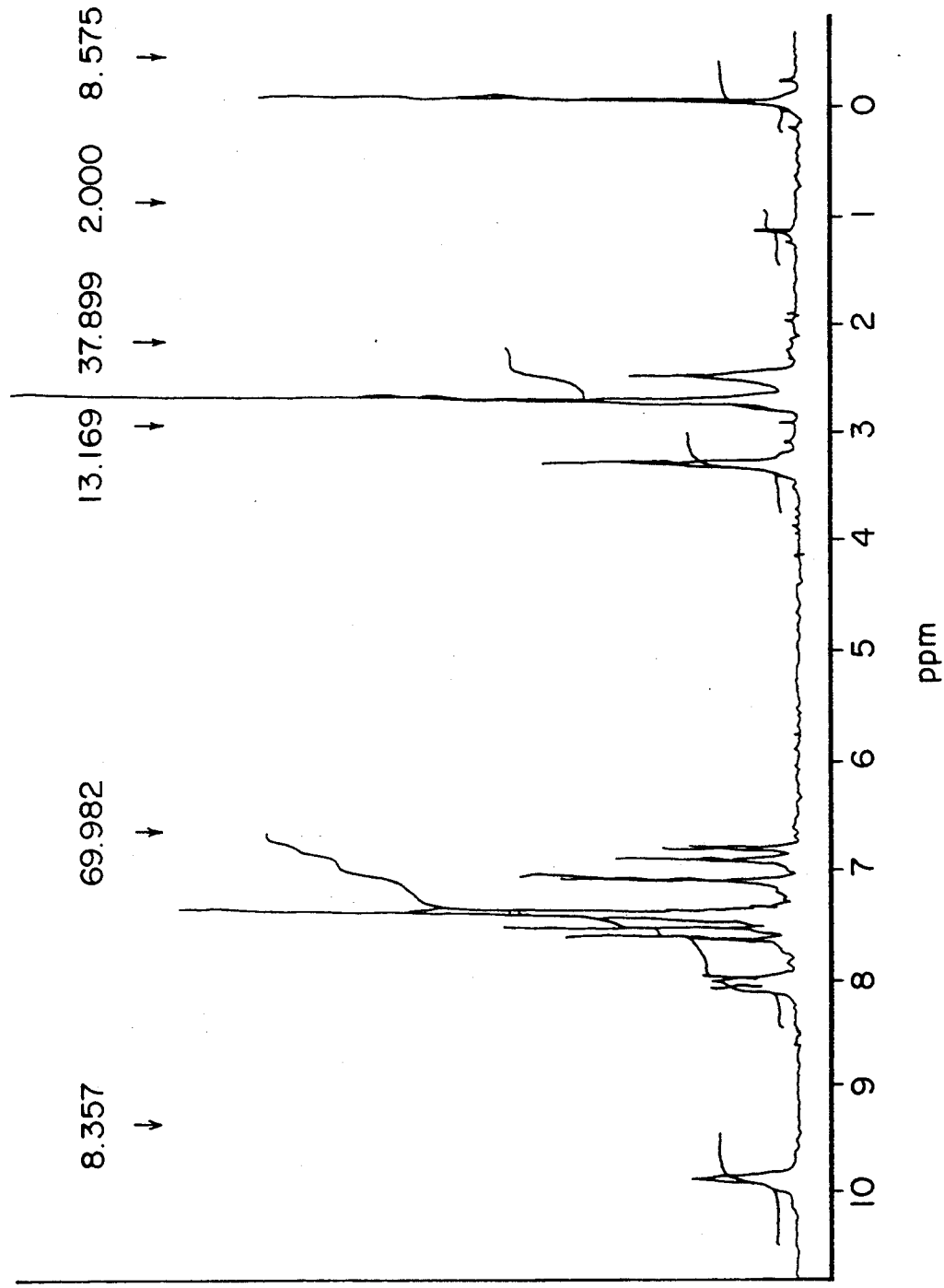
FIG. 11 is an NMR spectrum of the same.

NMR (FIG. 11, DMSO-d$_6$): 2.73 (s, 3H), 6.87 (dd, 1H), 7.11 (d, 1H), 7.42 (m, 3H), 7.64 (d, 1H), 8.06 (m, 1H), 9.86 (s, 1H)

MS (EI): 225 (M+), 196, 168, 156, 116, 91, 79, 51, 39

High resolution MS (EI): C$_{14}$H$_{11}$O$_2$N: Calculated: 225.0790. Observed 225.0764.

EXAMPLE 23

Luminescent assay of peroxidase in use of luminol and 2-ethoxycarbonyl-6-hydroxybenzoxazole 200 μl of a luminol solution (100 mM DMSO solution 10 μl/10ml 0.1 M tris-hydrochloride buffer solution, pH 8.5), 200 μl of the 2-ethoxycarbonyl-6-hydroxybenzoxazole obtained in Example 3 (100 mM DMSO solution 10 μl/10 ml, 0.1 M tris-hydrochloride buffer solution, pH 8.5) 10 μl of a horse radish peroxidase (HRP) solution [10,000 times dilution of 1111 unit/mg with a PBS buffer solution (pH 7.0) containing 1 g/l of BSA], and 10 μl of an aqueous solution of hydrogen peroxide (1000 times dilution of a 9.1 M aqueous solution) were introduced into a plastic cuvette, and the mixture was stirred for 3 seconds with a vortex mixer used, then the luminescent intensity after 1 minute was measured.

Next, 10 μl of a PBS buffer solution (pH 7.0) containing no HRP and the foregoing amounts of luminol and 2-ethoxycarbonyl-6-hydroxybenzoxazole were admixed and stirred, and the luminescent intensity after 1 minute was measured. The ratio of the former to the latter is shown, as signal-to-background ratio (NS ratio), in Table 6.

EXAMPLES 24 AND 25

As Examples 24 and 25, the procedure of Example 23 was followed except that isoluminol (Example 24) and N-(4-aminobutyl)-N-ethylisoluminol (abbreviated as ABEI in the following) (Example 25) were used in place of luminol in Example 23, and the luminescent intensities were measured, as shown in Table 6.

EXAMPLE 26

The procedure of Example 23 was followed except that 2-(3-bromophenyl)-6-hydroxybenzoxazole obtained in Example 21 was used in place of 2-ethoxycarbonyl-6-hydroxybenzoxazole in Example 23, and the luminescent intensity was measured, as shown in Table 6.

EXAMPLES 27 AND 28

As Examples 27 and 28, the procedure of Example 26 was followed except that isoluminol (Example 27) and ABEI (Example 28) were used in place of luminol in Example 26, and the luminescent intensities were measured, as shown in Table 6.

EXAMPLE 29

Similarly to Example 23 except that 2-chloromethyl-6-hydroxybenzoxazole obtained in Example 19 was used in place of 2-ethoxycarbonyl-6-hydroxybenzoxazole in Example 23, the luminescent intensity was measured, as shown in Table 6.

EXAMPLES 30 AND 31

As Examples 30 and 31, the luminescent intensities were measured similarly to Example 29 except that isoluminol (Example 30) and ABEI (Example 31) were used in place of luminol in Example 29, as shown in Table 6.

EXAMPLE 32

Similarly to Example 23 except that 2-(2-methylphenyl)-6-hydroxybenzoxazole obtained in Example 22 was used in place of 2-ethoxycarbonyl-6-hydroxybenzoxazole in Example 20, and luminescent intensity was measured, as shown in Table 6.

EXAMPLES 33 AND 34

As Examples 33 and 34, the luminescent intensities were measured similarly to Example 32 except that isoluminol (Example 33) and ABEI (Example 34) were used in place of luminol in Example 32, as shown in Table 6.

REFERENCES 16 TO 18

As References 16 to 18, luminescent intensities were measured similarly to Examples 23 to 25 except that 2-ethoxycarbonyl-6-hydroxybenzoxazole was not used, as shown in Table 6.

TABLE 6

Signal-to-background ratios (SN ratios) through combination of 2,3-dihydro-1,4-phthalazinedione (DPD) with enhancers

| | Enhancer | DPD | Luminescent intensity after 1 minute (relative value) | | |
|---|---|---|---|---|---|
| | | | +HRP | −HRP | SN ratio |
| Example 23 | 2-Ethoxycarbonyl-6-hydroxybenzoxazole | Luminol | 798373 | 86 | 9283.4 |
| Example 24 | 2-Ethoxycarbonyl-6-hydroxybenzoxazole | Isoluminol | 40492 | 28 | 1446.1 |
| Example 25 | 2-Ethoxycarbonyl-6-hydroxybenzoxazole | ABEI | 114290 | 32 | 3571.6 |
| Example 26 | 2-(3-Bromophenyl)-6-hydroxybenzoxazole | Luminol | 47370* | 246 | 192.6 |
| Example 27 | 2-(3-Bromophenyl)-6-hydroxybenzoxazole | Isoluminol | 602566 | 104 | 5793.9 |
| Example 28 | 2-(3-Bromophenyl)-6-hydroxybenzoxazole | ABEI | 780934 | 131 | 5961.3 |
| Example 29 | 2-Chloromethyl-6-hydroxybenzoxazole | Luminol | 360133 | 77 | 4677.1 |
| Example 30 | 2-Chloromethyl-6-hydroxybenzoxazole | Isoluminol | 5842 | 30 | 194.7 |
| Example 31 | 2-Chloromethyl-6-hydroxybenzoxazole | ABEI | 15880 | 32 | 496.3 |
| Example 32 | 2-(2-Methylphenyl)-6-hydroxybenzoxazole | Luminol | 1938090* | 78 | 24847.3 |
| Example 33 | 2-(2-Methylphenyl)-6-hydroxybenzoxazole | Isoluminol | 33186 | 49 | 677.3 |
| Example 34 | 2-(2-Methylphenyl)-6-hydroxybenzoxazole | ABEI | 56238 | 48 | 1171.6 |
| Reference 16 | None | Luminol | 867 | 461 | 1.9 |
| Reference 17 | None | Isoluminol | 694 | 122 | 5.7 |
| Reference 18 | None | ABEI | 344 | 167 | 1.2 |

*10 times value of the luminescent intensity obtained by 10 times dilution of HRP.

EXAMPLE 35

Synthesis of 2-(3-chlorophenyl)-6-hydroxybenzoxazole 4.5 ml (35.2 mmol) of 3-chlorobenzoyl chloride and 1.0 g (6.19 mmol) of 4-aminoresorcinol hydrochloride were introduced into a three-necked flask provided with a thermometer and a cooling condenser, and the mixture was heated at 170° to 235° C. for 1 hour, then the excessive acid chloride was removed by distillation. To the residue, 1.5 g (38.5 mmol) of NaOH, 20 ml of THF, 20 ml of water and 10 ml of ethanol were added, and the mixture was stirred at room temperature for about 2 hours. The reaction solution was extracted with ethyl acetate, the extract was washed with saturated sodium chloride water solution, and ethyl acetate was distilled off. Recrystallizing the residue with water/methanol/THF and drying the crystal, there was obtained 250 mg (1.02 mmol) of 2-(3-chlorophenyl)-6-hydroxybenzoxazole. The yield was 16.5%.

m.p.: 246.0° to 247.5° C.

Figure 12:
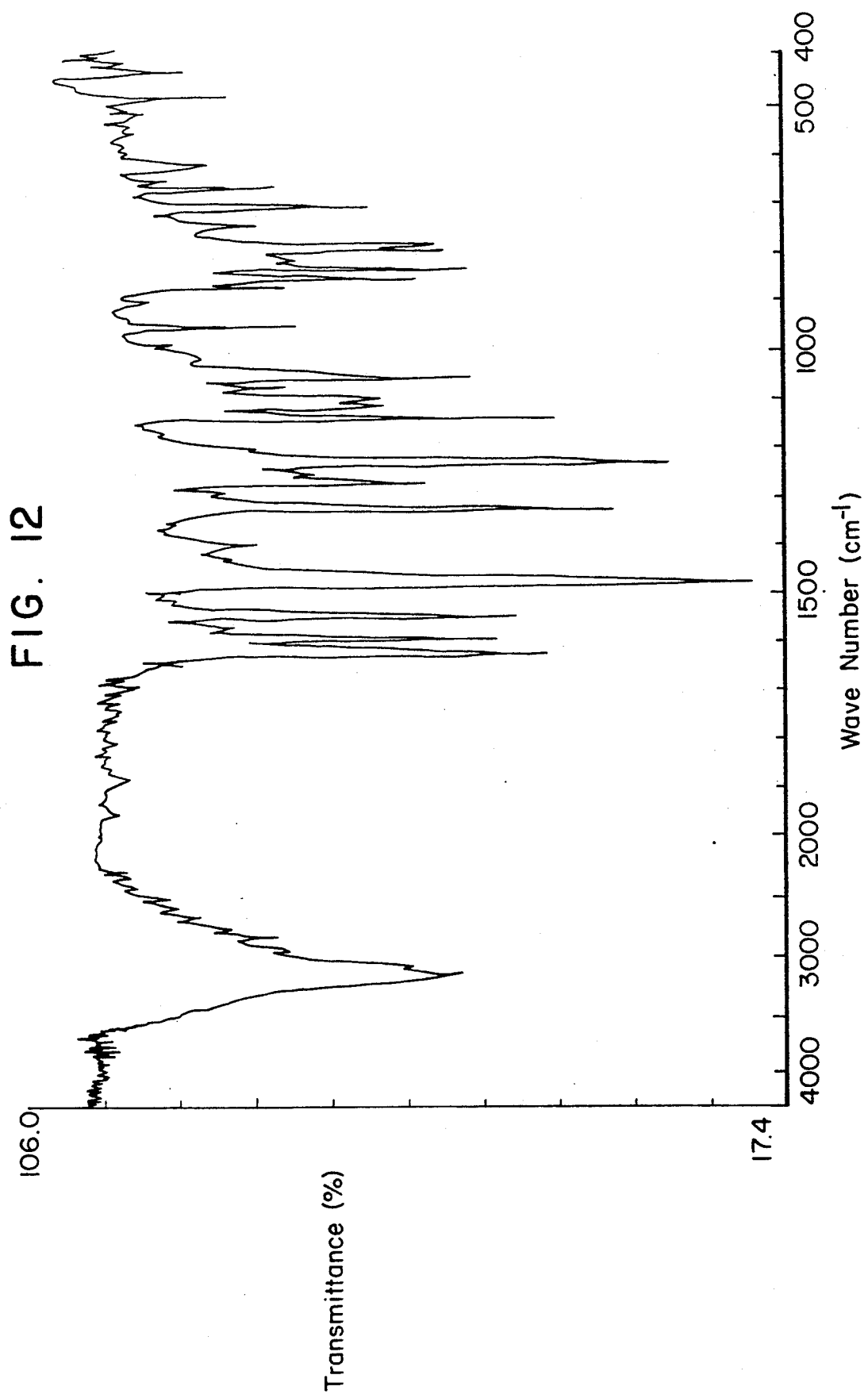
FIG. 12 is an IR spectrum of 2-(3-chlorophenyl)-6-hydroxybenzoxazole obtained in Example 35.

IR (FIG. 12, KBr, cm$^{-1}$): 3146, 1630, 1599, 1551, 1477, 1328, 1232, 1145, 1062, 835

Figure 13:
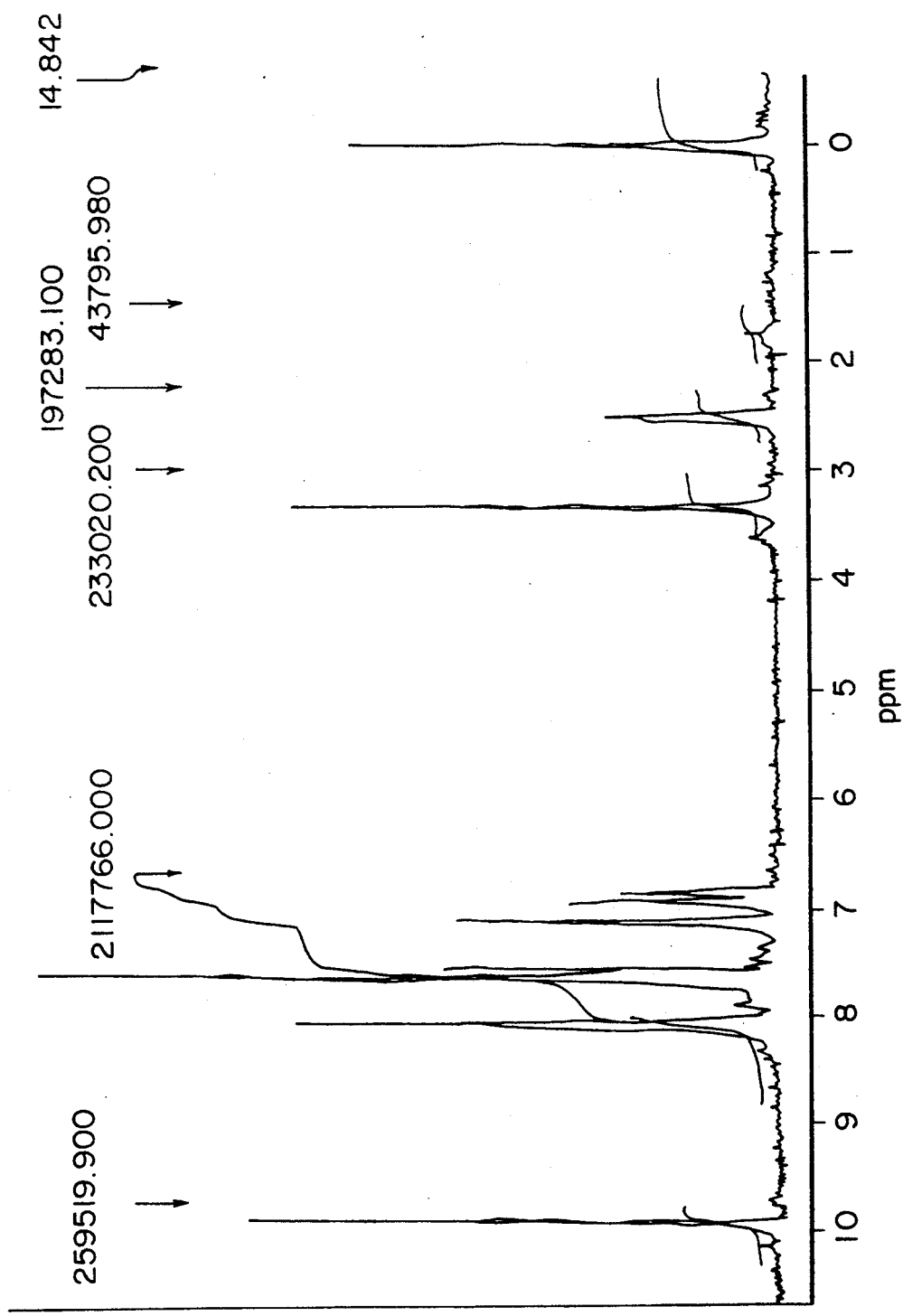
FIG. 13 is an NMR spectrum of the same.

NMR (FIG. 13, DMSO-d$_6$): 6.90 (dd, 1H), 7.12 (d, 1H), 7.61 (m, 3H), 8.06 (m, 2H), 9.94 (s, 1H)

MS (EI): 245 (M+), 247 (M++2), 138, 122, 80, 52

High resolution MS (EI): C$_{13}$H$_8$O$_2$NCl: Calculated: 245.0193. Observed 245.0218.

EXAMPLE 36

Synthesis of 2-(4-chlorophenyl)-6-hydroxybenzoxazole 25 g (142.8 mmol) of 4-chlorobenzoyl chloride and 3.0 g (18.6 mmol) of 4-aminoresorcinol hydrochloride were introduced into a three-necked flask provided with a thermometer and a cooling condenser, and the mixture was heated at 170° to 200° C. for 1 hour, then the excessive acid chloride was removed by distillation. To the residue, 8.4 g (210 mmol) of NaOH, 60 ml of THF, 60 ml of water and 30 ml of methanol were added, and the mixture was stirred at room temperature for about 2 hours. The reaction solution was extracted with ethyl acetate, the extract was washed with saturated sodium chloride water solution, and ethyl acetate was distilled off. Recrystallizing the residue with water/methanol/THF and drying the crystal, there was obtained 1.24 g (5.05 mmol) of 2-(4-chlorophenyl)-6-hydroxybenzoxazole. The yield was 27.2%.

m.p.: 272.8° to 273.5° C.

Figure 14:
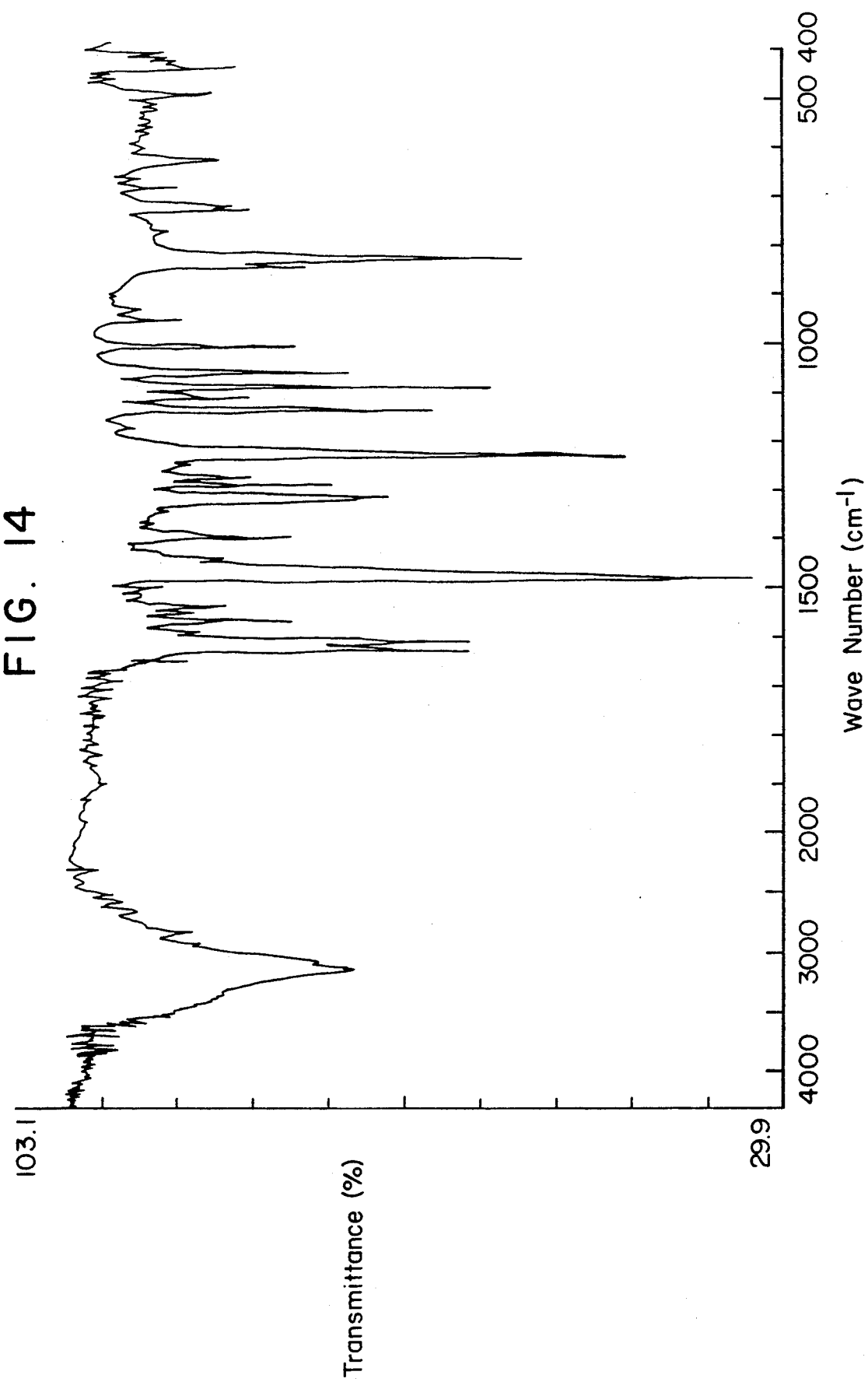
FIG. 14 is an IR spectrum of 2-(4-chlorophenyl)-6-hydroxybenzoxazole obtained in Example 36.

IR (FIG. 14, KBr, cm$^{-1}$): 3138, 1632, 1618, 1485, 1236, 1143, 832

Figure 15:
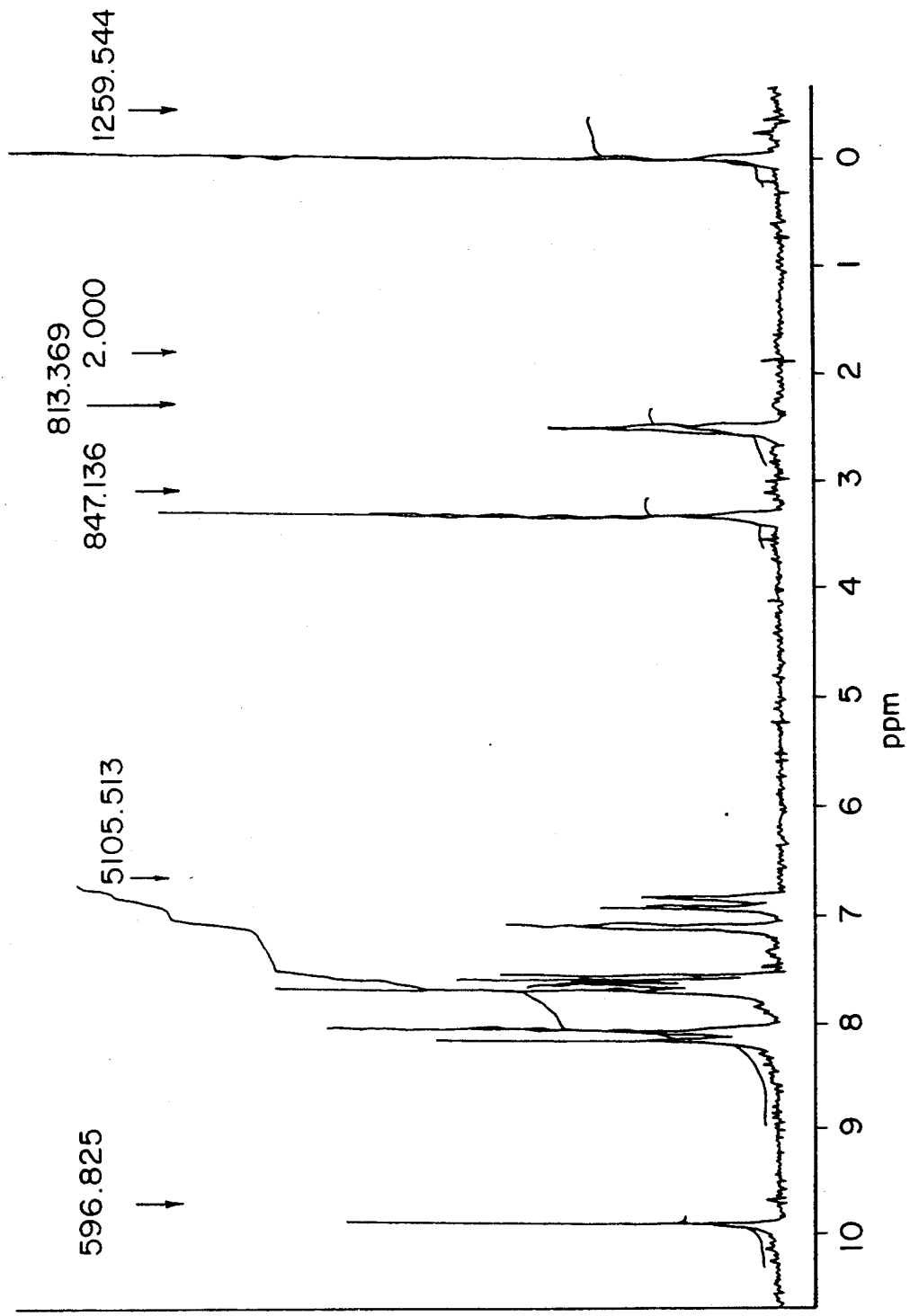
FIG. 15 is an NMR spectrum of the same.

NMR (FIG. 15, DMSO-d$_6$): 6.87 (dd, 1H), 7.11 (d, 1H), 7.62 (m, 3H), 8.13 (d, 2H), 9.90 (s, 1H)

MS(EI): 245 (M+), 247 (M++2), 138, 122

High resolution MS (EI): C$_{13}$H$_8$O$_2$NCl: Calculated 245.0178. Observed 245.0211.

EXAMPLE 37

Synthesis of 2-(2-naphthyl)-6-hydroxybenzoxazole 20 g (104.9 mmol) of 2-naphthyl chloride and 2.5 g (15.5 mmol) of 4-aminoresorcinol hydrochloride were introduced into a three-necked flask provided with a thermometer and a cooling condenser, and the mixture was heated at 135° to 205° C. for 1 hour, then excessive acid chloride was removed by distillation. To the residue, 8.3 g (207.5 mmol) of NaOH, 60 ml of THF, 60 ml of water and 30 ml of methanol were added, and the mixture was stirred at room temperature for about 2 hours. The reaction solution was extracted with ethyl acetate, the extract was washed with saturated sodium chloride water solution, and ethyl acetate was distilled off. Recrystallizing the residue with water/methanol/THF and drying the crystal, there was obtained 1.92 mg (7.36 mmol) of 2-(2-naphthyl)-6-hydroxybenzoxazole. The yield was 47.5%.

m.p.: 226.0° to 226.2° C.

Figure 16:
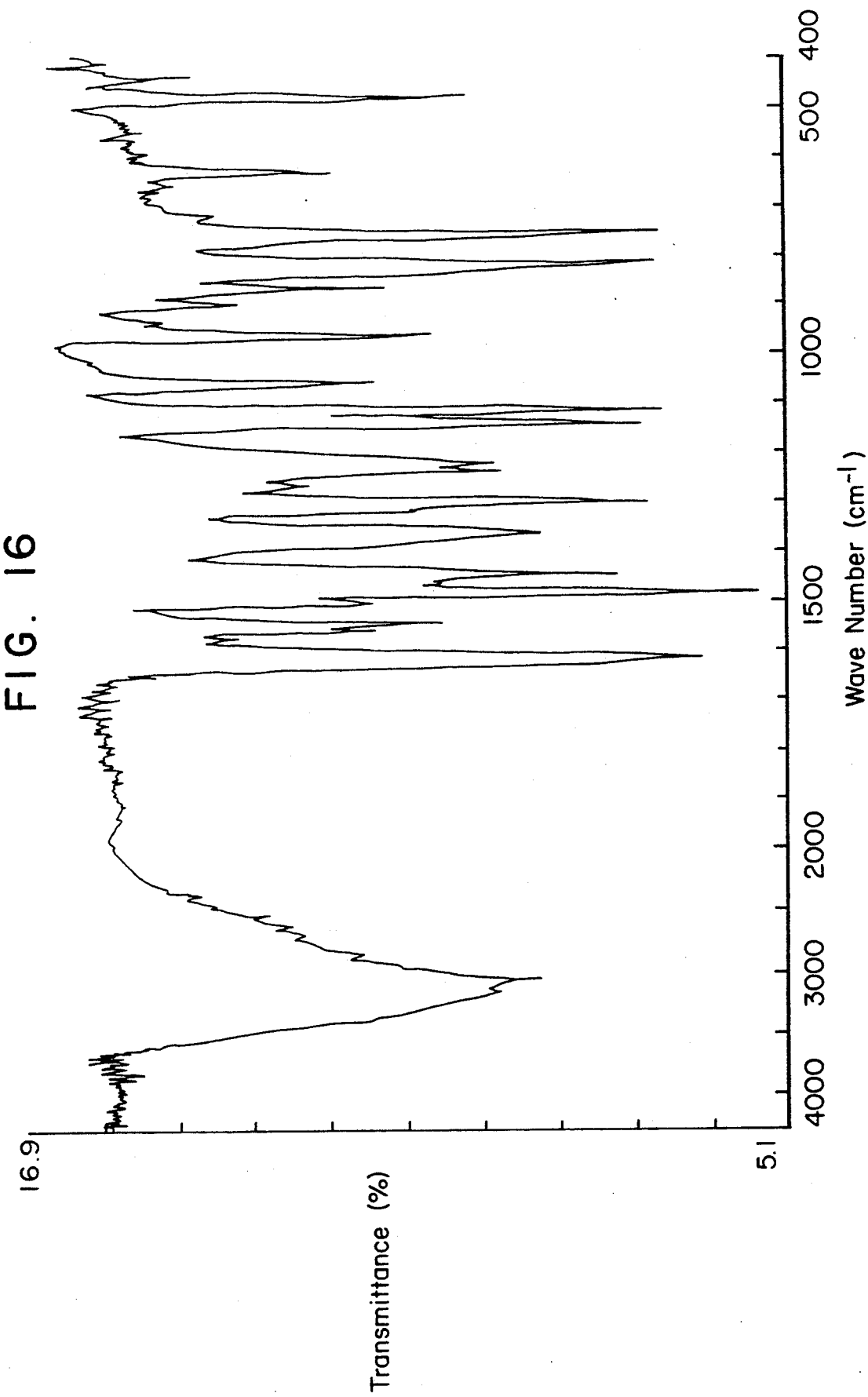
FIG. 16 is an IR spectrum of 2-(2-naphthyl)-6-hydroxybenzoxazole obtained in Example 37.

IR (FIG. 16, KBr, cm$^{-1}$): 3050, 1620, 1485, 1450, 1303, 1141, 1116, 816, 752

Figure 17:
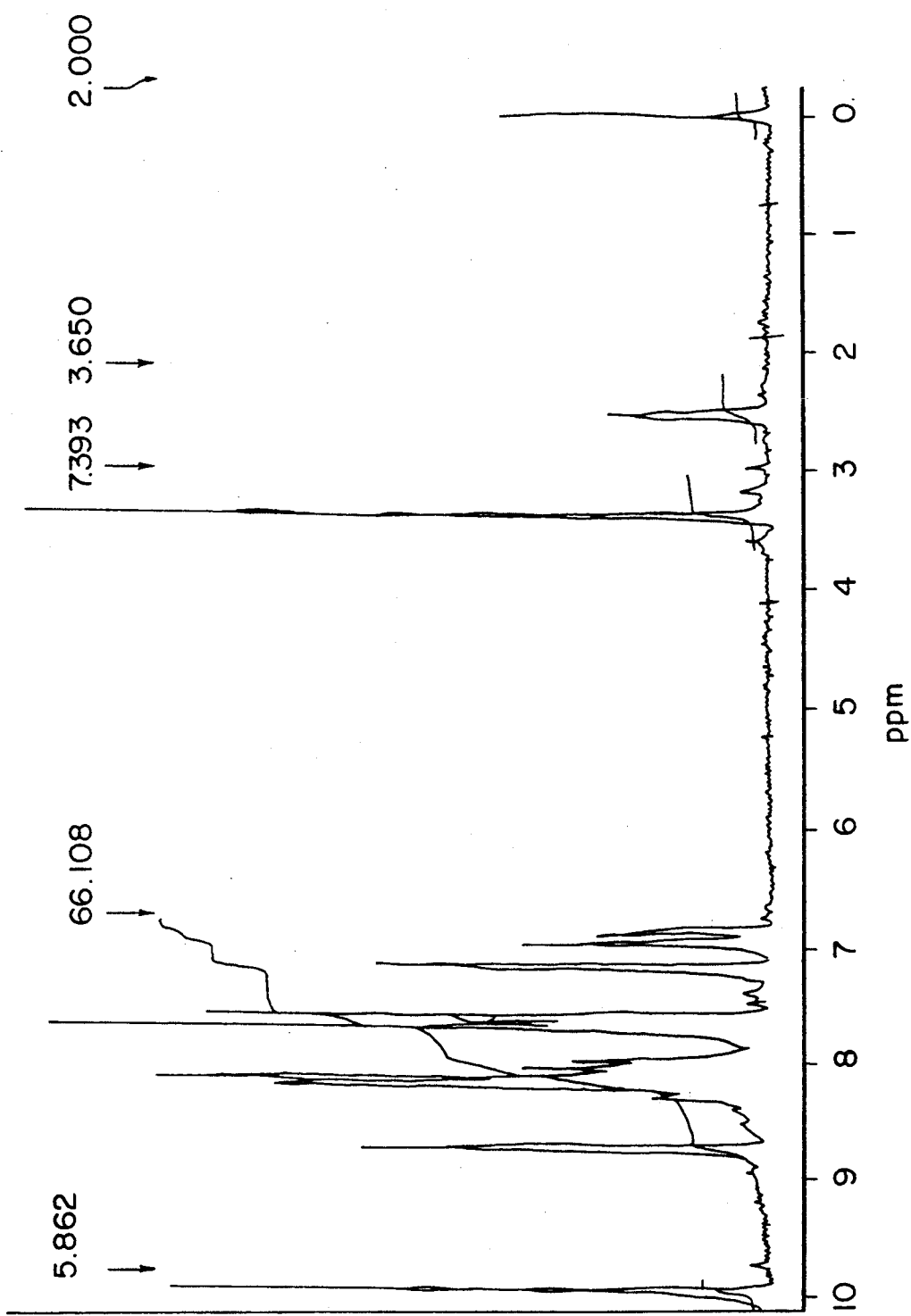
FIG. 17 is an NMR spectrum of the same.

NMR (FIG. 17, DMSO-d$_6$): 6.92 (dd, 1H), 7.17 (d, 1H), 7.64 (m, 3H), 8.08 (m, 4H), 8.74 (s, 1H), 9.92 (s, 1H)

MS (EI): 261 (M+), 130

High resolution MS (EI): C$_{17}$H$_{11}$O$_2$N: Calculated: 261.0825. Observed 261.0807.

EXAMPLE 38

Synthesis of 2-(2,4-dichlorophenyl)-6-hydroxybenzoxazole 9.9 ml (70.5 mmol) of 2,4-dichlorobenzoyl chloride and 2.0 g (12.4 mmol) of 4-aminoresorcinol hydrochloride were introduced into a three-necked flask provided with a thermometer and a cooling condenser, and the mixture was heated at 172° to 247° C. for 1 hour, then excessive acid chloride was removed by distillation. To the residue, 6.47 g (161.8 mmol) of NaOH, 60 ml of THF, 60 μl of water and 30 ml of methanol were added, and the mixture was stirred at room temperature for about 2 hours. The reaction solution was extracted with ethyl acetate, the extract was washed with saturated sodium chloride water solution, and ethyl acetate was distilled off. Recrystallizing the residue with water/methanol/THF and drying the crystal, there was obtained 915 mg (3.27 mmol) of 2-(2,4-dichlorophenyl)-6-hydroxybenzoxazole. The yield was 26.3%.

m.p.: 212.5° to 212.8° C.

Figure 18:
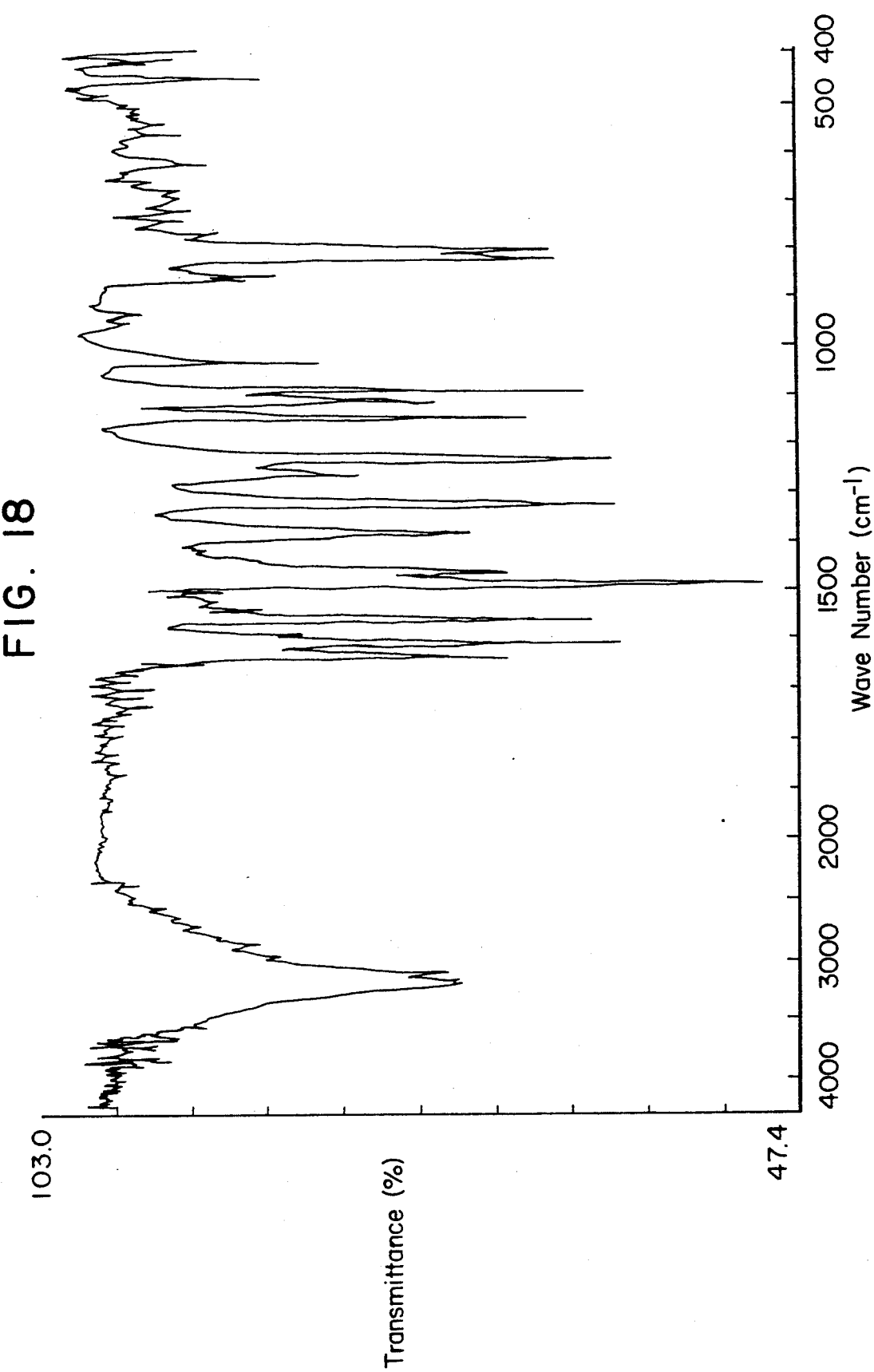
FIG. 18 is an IR spectrum of 2-(2,4-dichlorophenyl)-6-hydroxybenzoxazole obtained in Example 38.

IR (FIG. 18, KBr, cm$^{-1}$): 3150, 1638, 1611, 1564, 1489, 1464, 1325, 1232, 1094, 822, 808

Figure 19:
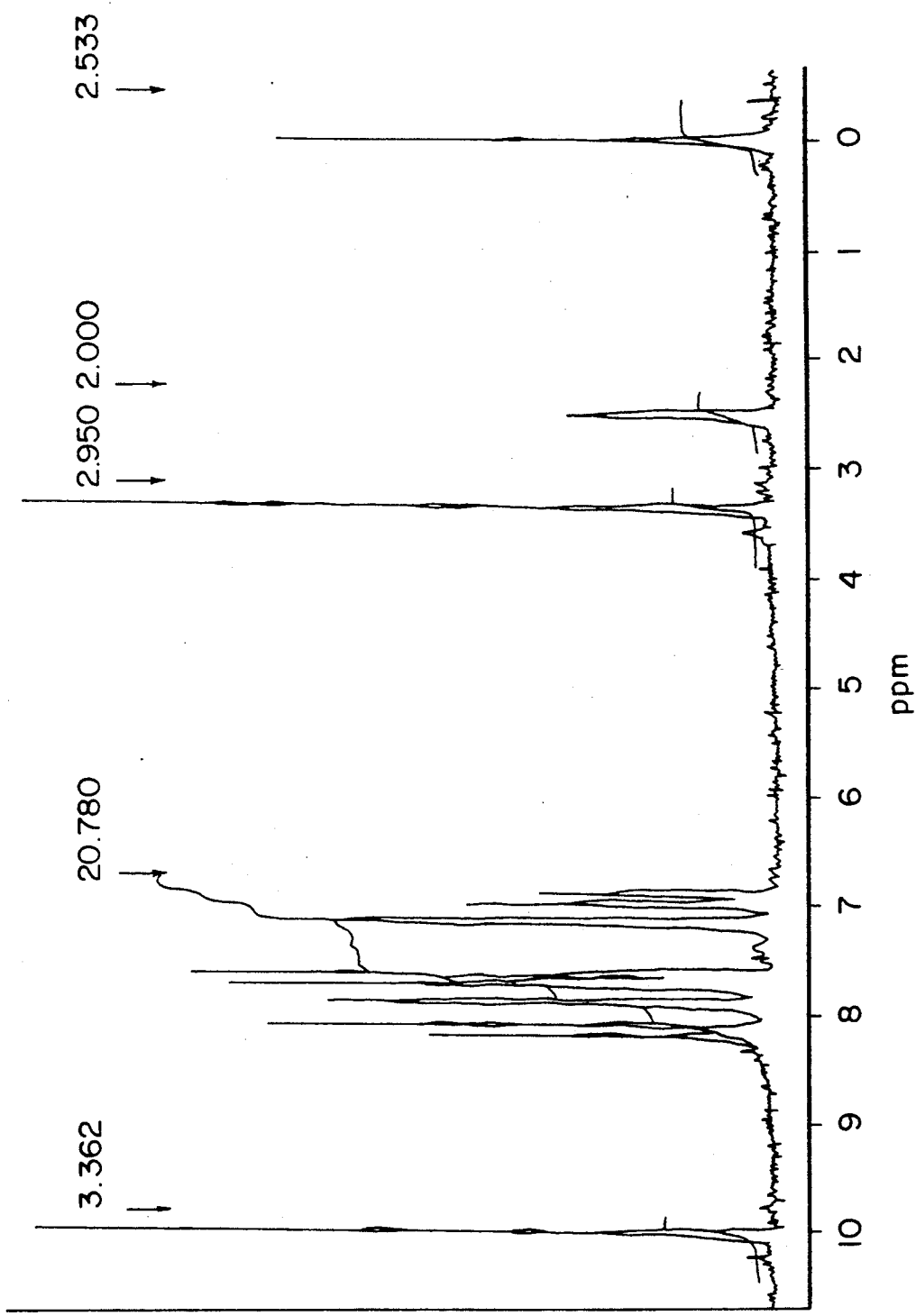
FIG. 19 is an NMR spectrum of the same.

NMR (FIG. 19, DMSO-d$_6$): 6.92 (dd, 1H), 7.11 (d, 1H), 7.66 (m, 2H), 7.85 (dd, 1H), 8.12 (d, 1H), 9.97 (s, 1H)

MS (EI): 279 (M+), 281 (M++2), 283 (M++4), 172, 139, 108, 80, 52

(EI): C

High resolution MS (EI): C$_{13}$H$_7$O$_2$HCl: Calculated: 278.9898. Observed 278.9876.

EXAMPLE 39

Luminescent assay of peroxidase in use of luminol and 2-(3-chlorophenyl)-6-hydroxybenzoxazole 200 μl of a luminol solution (100 mM DMSO solution 10 μl/10 ml, 0.1 M tris-hydrochloride buffer solution, pH 8.5), 200 μl of the 2-(3-chlorophenyl)-6-hydroxybenzoxazole solution obtained in Example 35 (100 mM DMSO solution 10 μl/10 ml, 0.1 M tris-hydrochloride buffer solution pH 8.5), 10 μl of a horse radish peroxidase (HRP) solution [10,000 times dilution of 1111 unit/mg with a PBS buffer solution (pH 7.0) containing 1 g/l of BSA] and 10 μl of a solution of hydrogen peroxide (1000 times dilution of a 9.1 M aqueous solution) were introduced into a plastic cuvette, and after stirring for 3 seconds with a vortex mixer, the luminescent intensity after 1 minute was measured.

Next, 10 μl of a PBS buffer solution (pH 7.0) not containing HRP and the foregoing amounts of luminol and -(3-chlorophenyl)-6-hydroxybenzoxazole were admixed and stirred, and the luminescent intensity after 1 minute was measured. The ratio of the former to the latter is shown, as signal-to-background ratio (SN ratio), in Table 7.

EXAMPLES 40 AND 41

As Examples 40 and 41, luminescent intensities were measured similarly to Example 39 except that in place of luminol in Example 39, isoluminol (Example 40) and N-(4-aminobutyl)-N-ethylisoluminol (Example 41) were used, as shown in Table 7.

EXAMPLE 42

Luminescent assay of peroxidase in use of luminol and 2-(4-chlorophenyl)-6-hydroxybenzoxazole 200 µl of a luminol solution (100 mM DMSO solution 10 µl/10 ml, 0.1 M tris-hydrochloride buffer solution pH 8.5, 200 µl of the 2-(4-chlorophenyl)-6-hydroxybenzoxazole solution obtained in Example 36 (100 mM DMSO solution 10 µl/10 ml, 0.1 M tris-hydrochloride buffer solution pH 8.5), 10 µl of a horse radish peroxidase (HRP) solution [10,000 times dilution of 1111 unit/g with a PBS buffer solution (pH 7.0) containing 1 g/l of BSA] and 10 µl of a solution of hydrogen peroxide (1000 times dilution of a 9.1 M aqueous solution) were introduced into a plastic cuvette, and after stirring for 3 seconds with a vortex mixer, the luminescent intensity after 1 minute was measured.

Next, 10 µl of a PBS buffer solution (pH 7.0) not containing HRP and the foregoing amount of luminol and 2-(4-chlorophenyl)-6-hydroxybenzoxazole were mixed and stirred, and the luminescent intensity after 1 minute was measured. The ratio of the former to the latter is shown, as signal-to-background ratio (SN ratio), in Table 7.

EXAMPLES 43 AND 44

As Examples 43 and 44, luminescent intensities were measured similarly to Example 42 except that in place of luminol in Example 42, isoluminol (Example 43) and N-(4-aminobutyl)-N-ethylisoluminol (ABEI) (Example 44) were used, as shown in Table 7.

EXAMPLE 45

Luminescent assay of peroxidase in use of luminol and 2-(2-naphthyl)-6-hydroxybenzoxazole 200 µl of a luminol solution (100 mM DMSO solution 10 µl/10 ml, 0.1 M tris-hydrochloride buffer solution pH 8.5), 200 µl of the 2-(2-naphthyl)-6-hydroxybenzoxazole solution obtained in Example 37 (100 mM DMSO solution 10 µl/10 ml, 0.1 M tris-hydrochloride buffer solution pH 8.5), 10 µl of a horse radish peroxidase (HRP) solution [10,000 times dilution of 1111 unit/mg with a PBS buffer solution (pH 7.0) containing 1 g/l of BSA] and 10 µl of a solution of hydrogen peroxide (1000 times dilution of a 9.1 M aqueous solution) were introduced into a plastic cuvette, and after stirring for 3 seconds with a vortex mixer, the luminescent intensity after 1 minute was measured.

Next, 10 µl of a PBS buffer solution (pH 7.0) not containing HRP and the foregoing amounts of luminol and 2-(2-naphthyl)-6-hydroxybenzoxazole were admixed and stirred, and the luminescent intensity after 1 minute was measured. The ratio of the former to the latter is shown, as signal-to-background ratio (SN ratio), in Table 7.

EXAMPLES 46 AND 47

As Examples 46 and 47, luminescent intensities were measured similarly to Example 45 except that in place of luminol in Example 45, isoluminol (Example 46) and N-(4-aminobutyl)-N-ethylisoluminol (Example 47) were used, as shown in Table 7.

EXAMPLE 48

Luminescent assay of peroxidase in use of luminol and 2-(2,4-dichlorophenyl)-6-hydroxybenzoxazole 200 µl of a luminol solution (100 mM DMSO solution 10 µl/10 ml, 0.1 M tris-hydrochloride buffer solution pH 8.5), 200 µl of the 2-(2,4-dichlorophenyl)-6-hydroxybenzoxazole solution obtained in Example 38 (100 mM DMSO solution 10 µl/10 ml, 0.1 M tris-hydrochloride buffer solution pH 8.5), 10 µl of a horse radish peroxidase (HRP) solution [10,000 times dilution of 1111 unit/g with a PBS buffer solution (pH 7.0) containing 1 g/l of BSA] and 10 µl of a solution of hydrogen peroxide (1000 times dilution of a 9.1 M aqueous solution) were introduced into a plastic cuvette, and after stirring for 3 seconds with a vortex mixer used, the luminescent intensity after 1 minute was measured.

Next, 10 µl of a PBS buffer solution (pH 7.0) not containing HRP and the foregoing amounts of luminol and 2-(2,4-dichlorophenyl)-6-hydroxybenzoxazole were mixed and stirred, and the luminescent intensity after 1 minute was measured. The ratio of the former to the latter is shown, as signal-to-background ratio (SN ratio), in Table 7.

EXAMPLES 49 AND 50

As Examples 49 and 50, luminescent intensities were measured similarly to Example 48 except that in place of luminol in Example 48, isoluminol (Example 49) and N-(4-aminobutyl)-N-ethylisoluminol (ABEI) (Example 50) were used, as shown in Table 7.

REFERENCES 19 to 21

As References 19 to 21, luminescent intensities were measured quite similarly to Examples 39 to 41 except that 2-(3-chlorophenyl)-6-hydroxybenzoxazole was not used, as shown in Table 7.

TABLE 7

| | Signal-to-background ratios (SN ratios) through combination of 2,3-dihydro-1,4-phthalizinedione (DPD) with enhancers | | | | |
|---|---|---|---|---|---|
| | | | Luminescent intensity after 1 minute (relative value) | | |
| | Enhancer | DPD | +HRP | −HRP | SN ratio |
| Example 39 | 2-(3-Chlorophenyl)-6-hydroxybenzoxazole | Luminol | 10253700* | 246 | 41681.7 |
| Example 40 | 2-(3-Chlorophenyl)-6-hydroxybenzoxazole | Isoluminol | 802093 | 85 | 9436.4 |
| Example 41 | 2-(3-Chlorophenyl)-6-hydroxybenzoxazole | ABEI | 1570750* | 100 | 15707.5 |
| Example 42 | 2-(4-Chlorophenyl)-6- | Luminol | 20805800** | 374 | 55630.5 |

TABLE 7-continued

Signal-to-background ratios (SN ratios) through combination of
2,3-dihydro-1,4-phthalizinedione (DPD) with enhancers

|  | Enhancer | DPD | Luminescent intensity after 1 minute (relative value) | | |
|---|---|---|---|---|---|
|  |  |  | +HRP | −HRP | SN ratio |
| Example 43 | 2-(4-Chlorophenyl)-6-hydroxybenzoxazole | Isoluminol | 582270 | 94 | 6194.4 |
| Example 44 | 2-(4-Chlorophenyl)-6-hydroxybenzoxazole | ABEI | 796149 | 96 | 8293.2 |
| Example 45 | 2-(2-Naphthyl)-6-hydroxybenzoxazole | Luminol | 6168950 | 350 | 17625.6 |
| Example 46 | 2-(2-Naphthyl)-6-hydroxybenzoxazole | Isoluminol | 446699 | 106 | 4214.1 |
| Example 47 | 2-(2-Naphthyl)-6-hydroxybenzoxazole | ABEI | 591743 | 115 | 5145.6 |
| Example 48 | 2-(2,4-Dichloro)-6-hydroxybenzoxazole | Luminol | 2923520** | 129 | 22662.9 |
| Example 49 | 2-(2,4-Dichloro)-6-hydroxybenzoxazole | Isoluminol | 706751 | 62 | 11399.2 |
| Example 50 | 2-(2,4-Dichloro)-6-hydroxybenzoxazole | ABEI | 935112 | 68 | 13751.6 |
| Reference 19 | None | Luminol | 583 | 377 | 1.5 |
| Reference 20 | None | Isoluminol | 463 | 160 | 2.9 |
| Reference 21 | None | ABEI | 273 | 174 | 1.6 |

*10 times value of the luminescent intensity obtained through 10 times dilution of HRP.
**20 times value of the luminescent intensity obtained through 20 times dilution of HRP.

EXAMPLE 51

Luminescent assay of CA15-3 antigen in use of 2-ethoxycarbonyl-6-hydroxybenzoxazole Diluting a CA15-3 antigen solution (615 U/ml) with a phosphate buffer solution (PBS) containing 0.25% bovine serum albumin into solutions of the concentrations of 300 U/ml, 200 U/ml, 100 U/ml, 50 U/ml, 25 U/ml and 0 U/ml (PBS containing 0.25 bovine serum albumin), these were taken as standard CA15-3 solutions.

The standard CA15-3 solutions of the foregoing concentrations were introduced to the wells of a tray (25 wells), each in 200 μl. Then, 300 μl of a peroxidase labeled anti-CA15-3 antibody (mouse) was added to the respective wells. To each well, an antibody coated bead, having the adhering liquid soaked up with filter paper, was added with a pincette.

Applying a tray cover seal, the tray was lightly tapped to mix the components in the respective wells, and each mixture was allowed to react at 25° C. for 2 hours. After completion of the reaction, the beads were washed 3 times, each time with 5 ml of physiological saline, with a bead washer used. After washing, each bead in the tray was transferred to a test tube then to a plastic cuvette for measurement with a luminometer.

100 μl of a luminol Na salt solution (18 times dilution of a solution of 12.6 mM, luminol Na salt/0.1 M tris-hydrochloride buffer solution pH 8.5 with the same buffer solution), 100 μl of a 2-ethoxycarbonyl-6-hydroxybenzoxazole solution (100 mM DMSO solution 10 μl/10 ml, 0.1 M tris-hydrochloride buffer solution pH 8.5) and 100 μl of a solution of hydrogen peroxide (18 times dilution of 16.2 μM hydrogen peroxide/0.01 M disodium hydrogen phosphate-citric acid buffer solution pH 5.2 with the same buffer solution) were added to a plastic vial, and after heating at 37° C. for 10 minutes, the luminescence was measured for 60 seconds. 1/6 Values of the cumulative values of luminescent intensities of from 50 seconds to 60 seconds are shown in Table 8.

Figure 20:
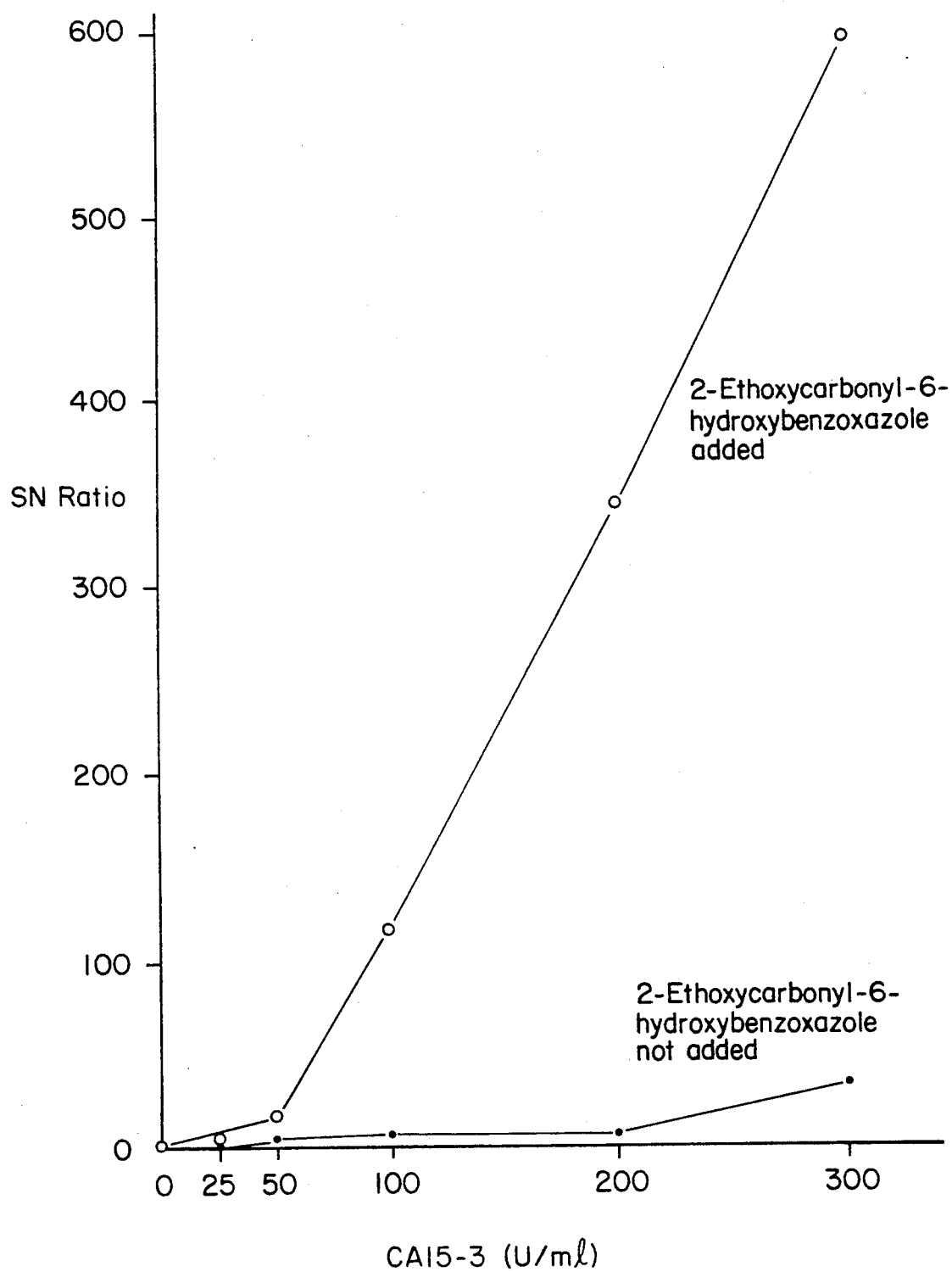
FIG. 20 shows the values of SN ratio obtained in Example 51 and Reference 22.

Then, the ratios of the 1/6 values of the cumulative values of luminescent intensities of from 50 seconds to 60 seconds of the standard CA15-3 solutions (300 U/ml, 200 U/ml, 100 U/ml, 50 U/ml and 25 U/ml) to the 1/6 value of the cumulative value of luminescent intensity of from 50 seconds to 60 seconds of 0 U/ml (SN ratios) were obtained, as shown in Table 8 and FIG. 20.

Reference 22

According to the procedure of Example 35 except that 2-ethoxycarbonyl-6-hydroxybenzoxazole was not used, the luminescent intensities and SN ratios were obtained, as shown in Table 8 and FIG. 20.

TABLE 8

Analysis of CA15-3; 1/6 Values of the cumulative values of luminescent intensities of from 50 seconds to 60 seconds

|  | Enhancer |  | CA15-3 (U/ml) | | | | | |
|---|---|---|---|---|---|---|---|---|
|  |  |  | 0 | 25 | 50 | 100 | 200 | 300 |
| Example 51 | 2-Ethoxycarbonyl-6-hydroxybenzoxazole | Luminescent intensity (relative value) | 151 | 763 | 2729 | 18333 | 54503 | 94172 |
|  |  | SN ratio | 1 | 4.86 | 17.4 | 117 | 347 | 600 |
| Reference 22 | None | Luminescent intensity (relative value) | 250 | 329 | 397 | 968 | 1422 | 8625 |
|  |  | SN ratio | 1 | 1.32 | 1.59 | 3.87 | 5.69 | 34.5 |

As described in the foregoing, the method of luminescence analysis of the present invention enables high sensitivity and prompt determination of substances.

We claim:

1. A process for detecting or determining the presence of a substance by the chemiluminescence produced through reaction of (a) peroxidase or a derivative thereof, (b) an oxidant and (c) luminol or isoluminol or a derivative thereof, wherein said chemiluminescence-inducing reaction is carried out in the presence of at least one compound selected from the group consisting of 2-hydroxy-9-fluorenone, the compound

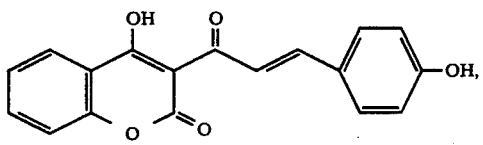

and oxazole derivatives of the formula

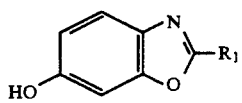

wherein $R_1$ represents hydrogen, $C_nH_{2n+1}$, $XC_nH_{2n}$, $C_nH_{2n+1}CO_2$, a phenyl group, a naphthyl group, $C_nH_{2n+1}C_6H_4$, $YC_6H_4$, or $XYC_6H_3$; wherein n is a positive integer from 1 to 4, X is F, Cl, Br, or I, and Y is F, Cl, Br, I, or a phenyl group.

2. The process according to claim 1, wherein $R_1$ is selected from the group consisting of fluoromethyl, 1-chloromethyl, bromomethyl, iodomethyl, 1-fluoromethyl, 2-fluoromethyl, 1-chloroethyl, 2-chloroethyl, 1-bromoethyl, 2-bromoethyl, 1-iodoethyl, 2-iodoethyl, 1-fluoropropyl, 2-fluoropropyl, 3-fluoropropyl, 1-fluoro-1-methylethyl, 2-fluoro-1-methylethyl, 1-chloropropyl, 2-chloropropyl, 3-chloropropyl, 1-chloro-1-methylethyl, 2-chloro-1-methylethyl, 1-bromopropyl, 2-bromopropyl, 3-bromopropyl, 1-bromo-1-methylethyl, 2-bromo-1-methylethyl, 1-iodopropyl, 2-iodopropyl, 3-iodopropyl, 1-iodo-1-methylethyl, 2-iodo-1-methylethyl, 1-fluorobutyl, 2-fluorobutyl, 3-fluorobutyl, 4-fluorobutyl, 1-fluoro-1-methylpropyl, 2-fluoro-1-methylpropyl, 3-fluoro-1-methylpropyl, 1-fluoromethylpropyl, 1-fluoro-2-methylpropyl, 2-fluoro-2-methylpropyl, 3-fluoro-2-methylpropyl, 1-fluoromethyl-1,1-dimethylmethyl, 1-chlorobutyl, 2-chlorobutyl, 3-chlorobutyl, 4-chlorobutyl, 1-chloro-1-methylpropyl, 2-chloro-1-methylpropyl, 3-chloro-1-methylpropyl, 1-chloromethylpropyl, chloro-2-methylpropyl, 2-chloro-2-methylpropyl, 3-chloro-2-methylpropyl, 1-chloromethyl-1,1-dimethylmethyl, 1-bromobutyl, 2-bromobutyl, 3-bromobutyl, 4-bromobutyl, 1-bromo-1methylpropyl, 2-bromo-1-methylpropyl, 3-bromo-1-methylpropyl, 1-bromomethylpropyl, 1-bromo-2methylpropyl, 2-bromo-2-methylpropyl, 3-bromo-2-methylpropyl, 1-bromomethylmethyl-1,1-dimethylmethyl, 1-iodobutyl, 2-iodobutyl, 3-iodobutyl, 4-iodobutyl, 1-iodo-1-methylpropyl, 2-iodo-1-methylpropyl, 3-iodo-1methylpropyl, 1-iodo-2-methylpropyl, 2-iodo-2-methylpropyl, 3-iodo-2-methylpropyl and 1-iodomethyl-1,1-dimethylmethyl.

3. The process according to claim 1, wherein $R_1$ is selected from the group consisting of methoxycarbonyl, ethoxycarbonyl, propoxycarbonyl, 1-methylethoxycarbonyl, butoxycarbonyl, 1-methylpropoxycarbonyl, 2-methylpropoxycarbonyl and 1,1-dimethylethoxycarbonyl.

4. The process according to claim 1, wherein $R_1$ is selected from the group consisting of 2-methylphenyl, 3-methylphenyl, 4-methylphenyl, 2-ethylphenyl, 3-ethylphenyl, 4-ethylphenyl, 2-propylphenyl, 3-propylphenyl, 4-propylphenyl, 2-(1-methylphenyl), 3-(1-methylethyl), 4-(1methylethyl), 2-butylphenyl, 3-butylphenyl, 4-butylphenyl, 2-(1-methylpropyl)phenyl, 3-(1-methylpropyl)phenyl, 4-(1-methylpropyl)phenyl, 2-(2-methylpropyl)phenyl, 3-(2-methylpropyl)phenyl, 4-(2-methylpropyl)phenyl, 2-(1,1-dimethylethyl)phenyl, 3-(1,1-dimethylethyl)phenyl and 4-(1,1-dimethylethyl)-phenyl.

5. The process according to claim 1, wherein $R_1$ is selected from the group consisting of 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2-iodophenyl, 3-iodophenyl and 4-iodophenyl.

6. The process according to claim 1, wherein $R_1$ is selected from the group consisting of 2,4-dichlorophenyl and 3,5-dichlorophenyl.

7. The process according to claim 1, wherein $R_1$ is selected from the group consisting of hydrogen, a methyl group, a chloromethyl group, an ethoxycarbonyl group, a phenyl group, a bromophenyl group, a methylphenyl group, a chlorophenyl group, a naphthyl group and a dichlorophenyl group.

8. An oxazole derivative having the formula

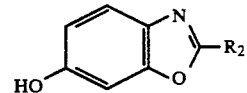

wherein $R_2$ is selected from the group consisting of $XC_nH_{2n}$, $C_nH_{2n+1}CO_2$, a naphthyl group, $C_nH_{2n+1}C_6H_4$, $Y_6H_4$ and $XYC_6H_3$, wherein n is a positive integer of 1 to 4, X is F, Cl, Br, or I, and Y is F, Cl, Br, I, or a phenyl group.

9. The oxazole derivative according to claim 8, wherein $R_2$ is selected from the group consisting of fluoromethyl, 1-chloromethyl, bromomethyl, iodomethyl, 1-fluoromethyl, 2-fluoromethyl, 1-chloroethyl, 2-chloroethyl, 1-bromoethyl, 2-bromoethyl, 1-iodoethyl, 2-iodoethyl, 1-fluoropropyl, 2-fluoropropyl, 3-fluoropropyl, 1-fluoro-1-methylethyl, 2-fluoro-1-methylethyl, 1-chloropropyl, 2-chloropropyl, 3-chloropropyl, 1-chloro-1-methylethyl, 2-chloro-1-methylethyl, 1-bromopropyl, 2-bromopropyl, 3-bromopropyl, 1-bromo-1-methylethyl, 2-bromo-1-methylethyl, 1-iodopropyl, 2-iodopropyl, 3-iodopropyl, 1-iodo-1-methylethyl, 2-iodo-1-methylethyl, 1-fluorobutyl, 2-fluorobutyl, 3-fluorobutyl, 4-fluorobutyl, 1-fluoro-1-methylpropyl, 2-fluoro-1-methylpropyl, 3-fluoro-1-methylpropyl, 1-fluoromethylpropyl, 1-fluoro-2-methylpropyl, 2-fluoro-2-methylpropyl, 3-fluoro-2-methylpropyl, 1-fluoromethyl-1,1-dimethylmethyl, 1-chlorobutyl, 2-chlorobutyl, 3-chlorobutyl, 4-chlorobutyl, 1-chloro-1-methylpropyl, 2-chloro-1-methylpropyl, 3-chloro-1-methylpropyl, 1-chloromethylpropyl, 1-chloro-2-methylpropyl, 2-chloro-2-methylpropyl, 3-chloro-2-methylpropyl, 1-chloromethyl-1,1-dimethylmethyl, 1-bromobutyl, 2-bromobutyl, 3-bromobutyl, 4-bromobutyl, 1-bromo-1methylpropyl, 2-bromo-1-methylpropyl, 3-bromo-1-methylpropyl, 1-bromomethylpropyl, 1-bromo-2methylpropyl, 2-bromo-2-methylpropyl, 3-bromo-2-methylpropyl, 1-bromomethylmethyl-1,1-dimethylmethyl, 1-iodobutyl, 2-iodobutyl, 3-iodobutyl, 4-iodobutyl, 1-iodo-1-methylpropyl, 2-iodo-1-methylpropyl, 3-iodo-1methylpropyl, 1-iodo-2-methylpropyl, 2-iodo-2-methylpropyl, 3-iodo-2-methylpropyl and 1-iodomethyl-1,1-dimethylmethyl.

10. The oxazole derivative according to claim 8, wherein $R_1$ is selected from the group consisting of methoxycarbonyl, ethoxycarbonyl, propoxycarbonyl, 1-methylethoxycarbonyl, butoxycarbonyl, 1-methylpropoxycarbonyl, 2-methylpropoxycarbonyl and 1,1-dimethyl-ethoxycarbonyl.

11. The oxazole derivative according to claim 8, wherein $R_1$ is selected from the group consisting of 2-methylphenyl, 3-methylphenyl, 4-methylphenyl, 2-ethylphenyl, 3-ethylphenyl, 4-ethylphenyl, 2-propylphenyl, 3-propylphenyl, 4-propylphenyl, 2-(1-methylethyl), 3-(1-methylethyl), 4-(1-methylethyl), 2-butylphenyl, 3-butylphenyl, 4-butylphenyl, 2-(1-methylpropyl)phenyl, 3-(1-methylpropyl)phenyl, 4-(1-methylpropyl)phenyl, 2-(2-methylpropyl)phenyl, 3-(2-methylpropyl)phenyl, 4-(2-methylpropyl)phenyl, 2-(1,1-dimethylethyl)phenyl, 3-(1,1-dimethylethyl)phenyl and 4-(1,1-dimethylethyl)phenyl.

12. The oxazole derivative according to claim 8, wherein $R_1$ is selected from the group consisting of 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2-iodophenyl, 3-iodophenyl and 4-iodophenyl.

13. The oxazole derivative according to claim 8, wherein $R_1$ is selected from the group consisting of 2,4-dichlorophenyl and 3,5-dichlorophenyl.

14. The oxazole derivative according to claim 8, wherein $R_2$ is selected from the group consisting of a chloromethyl group, an ethoxycarbonyl group, a bromophenyl group, a chlorophenyl group, a naphthyl group, a dichlorophenyl group and a methylphenyl group.

* * * * *